United States Patent
Tsoukalis

(10) Patent No.: US 11,160,921 B2
(45) Date of Patent: Nov. 2, 2021

(54) PUMP INFUSION SYSTEM

(71) Applicant: MICREL Medical Devices S.A., Gerakas (GR)

(72) Inventor: Achilleas Tsoukalis, Anavyssos Attiki (GR)

(73) Assignee: MICREL Medical Devices S.A., Gerakas (GR)

( * ) Notice: Subject to any disclaimer, the term of this patent is extended or adjusted under 35 U.S.C. 154(b) by 0 days.

(21) Appl. No.: 15/457,390

(22) Filed: Mar. 13, 2017

(65) Prior Publication Data
US 2017/0258986 A1  Sep. 14, 2017

(30) Foreign Application Priority Data

Mar. 11, 2016  (EP) ..................................... 16159824

(51) Int. Cl.
*A61M 5/142* (2006.01)
*G16H 10/60* (2018.01)
(Continued)

(52) U.S. Cl.
CPC ........ *A61M 5/14244* (2013.01); *G16H 10/60* (2018.01); *G16H 20/17* (2018.01);
(Continued)

(58) Field of Classification Search
CPC ....... A61M 2005/14208; A61M 5/1723; G06F 19/3468
See application file for complete search history.

(56) References Cited

U.S. PATENT DOCUMENTS 5,685,844 A * 11/1997 Marttila ................ A61M 5/172
604/65
7,108,680 B2 * 9/2006 Rohr .................. A61B 5/14503
604/151
(Continued)

FOREIGN PATENT DOCUMENTS

EP  1069921  1/2001
EP  1385420  2/2004
(Continued)

OTHER PUBLICATIONS

EP Search Report from EP App. No. 17160688.2 dated Jul. 20, 2017, 16 pages.

*Primary Examiner* — William R Carpenter
(74) *Attorney, Agent, or Firm* — Bookoff McAndrews, PLLC

(57) ABSTRACT

An infusion pump system comprises a pump for infusing a drug into a patient, a storing unit for storing therapy data, drug data, protocol data, profile data, care type data, and feedback data received from said pump and/or other sources including information about particularities of therapies already carried out or currently running, an input unit for selecting therapy data, drug data, profile data, and care type data, an associating unit for associating the selected therapy data, drug data, profile data and care type data provided by said input unit and further adapted to determine based on said association specific protocol data and specific feedback data, wherein said storing unit also stores said association with said specific protocol data and said specific feedback data; and an output unit for outputting said specific protocol data with said specific feedback data.

29 Claims, 15 Drawing Sheets

(51) Int. Cl.
    *G16H 40/63*     (2018.01)
    *G16H 20/17*     (2018.01)
    *G16H 70/40*     (2018.01)
    *G16H 10/20*     (2018.01)
    *A61M 5/172*     (2006.01)
    *G16H 70/20*     (2018.01)
    *G16H 70/60*     (2018.01)

(52) U.S. Cl.
    CPC ............ *G16H 40/63* (2018.01); *G16H 70/40* (2018.01); *A61M 5/142* (2013.01); *A61M 5/1723* (2013.01); *A61M 2005/14208* (2013.01); *A61M 2205/18* (2013.01); *A61M 2205/505* (2013.01); *A61M 2205/52* (2013.01); *A61M 2205/609* (2013.01); *A61M 2205/6072* (2013.01); *G16H 10/20* (2018.01); *G16H 70/20* (2018.01); *G16H 70/60* (2018.01)

(56) References Cited

U.S. PATENT DOCUMENTS

| | | | |
|---|---|---|---|
| 8,172,798 B2 | 5/2012 | Hungerford et al. | |
| 8,551,038 B2 | 10/2013 | Tsoukalis | |
| 8,894,631 B2 | 11/2014 | Mctaggart et al. | |
| 2001/0025156 A1* | 9/2001 | Bui | A61M 5/1723 604/66 |
| 2005/0277912 A1* | 12/2005 | John | G16H 20/17 604/890.1 |
| 2011/0184264 A1* | 7/2011 | Galasso | G01N 27/327 600/347 |
| 2012/0016295 A1* | 1/2012 | Tsoukalis | G16H 20/17 604/66 |
| 2012/0172802 A1 | 7/2012 | Blomquist | |
| 2013/0012880 A1* | 1/2013 | Blomquist | A61M 5/142 604/151 |
| 2015/0151051 A1 | 6/2015 | Tsoukalis | |
| 2016/0000994 A1 | 1/2016 | Blomquist | |
| 2016/0051750 A1 | 2/2016 | Tsoukalis | |

FOREIGN PATENT DOCUMENTS

| | | |
|---|---|---|
| EP | 2410448 | 1/2012 |
| EP | 2881875 | 6/2015 |
| EP | 2987517 | 2/2016 |
| WO | WO2016196098 | 12/2016 |

\* cited by examiner

Fig. 3A

Therapy Monitoring

Patient Name, therapy, Care Type, Drug, pump, protocol

Monitor:
pump function (run stop, connected Y/N, battery etc.),
protocol progress (VTBI, Rate, Bolus etc.), pump alarms and warnings
Feedback responses-values (VAS pain score in Palliative Care type or VAS @ Mobilization + VAS @ rest + numbness + motor blockage in Post Op pain Care type, etc.) and other feedback non question based (bolus asked vs Bolus given – reject ratio % in palliative care, or infusions No. + Occlusion alarms + average downstream pressure + max pressure + Kcal/day in PN Care type etc.)
Timeline graph of observations (Rate, bolus, nutritional content per time etc.) + feedback (VAS score, question answers) per time
Therapy progress specific visualizations

Fig. 3f

Pump communication

- Regular Pump status (during infusion/standby)
- Regular pump location (Wi-Fi hotspot sniffing intensities)
- Alarms at event
- Drug library upload (including relevant to pump protocols and group protocols, therapy feedback questions)
- Care Plan upload to pump
- Remote programming (if allowed) and limits
- Pump scans IDs of drug & patient and takes SR from server
- Scans patient and gets pending protocols from server
- App gets position from Wi-Fi and shows only pumps in area (each positioned through Wi-Fi sniffing from server)
- Patient face photo analyzed and sends back (Name, Age, Weight, Genre) to pump together with therapy registered and pending protocols

Fig. 3g

Stakeholders Pages

Social Security Page
Therapy compliance
Reimbursement evidence

Pharmaceutical Company Page
Drug consumption / country/ Health Organization
Drug side effects big data clinical trial
Patient compliance / drug
Marketing info

Mobile Apps
Patient
Relatives
Caregivers

Activity summary of last     48hrs ▾
Patient bolus activity
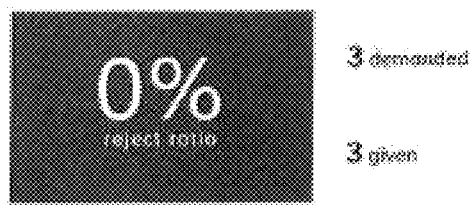
3 demanded
3 given
Summary of observations
Activity summary of last     4hrs ▾
VAS at mobilization
6 ↑
3h 12 min ago
8 max
3 min
Numbness
Positive
3h 12 min ago
1 positive
0 negative
Activity summary of last     4hrs ▾
VAS at mobilization
6 ↑
3h 12 min ago
8 max
3 min
Numbness
Positive
3h 12 min ago
1 positive
0 negative
Fig. 4a

PUMP INFUSION SYSTEM

TECHNICAL FIELD

The present invention relates to an infusion pump system comprising a pump adapted to be attached to a patient and to cause infusion of a drug into the patient's body. Further, the infusion pump system can also comprise a plurality of pumps.

BACKGROUND

Infusion pumps are used to deliver a selected drug to a patient in accordance with a specific protocol which defines a specific drug delivery and application, e.g. with a predetermined rate and a predetermined dose, to a patient. Usually the protocol is programmed into the infusion pump. Programming and managing infusion pumps can be difficult in particular since an infusion pump can be programmed in accordance with different protocols for different therapies and different locations.

In the prior art, infusion pump systems have been developed which use so-called smart pumps and a drug library. The drug library is a database which can be embedded in the pump, in a personal computer and/or in a remote server (e.g., cloud) and is used to provide protocols and associated soft and hard infusion limits, wherein soft limits can be overwritten and hard limits cannot be overwritten. The protocols and limits are given as output to a query to the database by using search terms such as "therapy", "drug" and "profile". These systems allow a reduction of medication errors by identifying a therapy which requires specific drugs and specific limits and/or by identifying the relevant care area and patient's attributes. However, in particular in view of the huge extent of the drug library which offers a high number of drugs, there remains a question about therapy outcome.

SUMMARY OF THE INVENTION

It is an object of the present invention to provide an improved infusion pump system in order to overcome drawbacks of the prior art.

In order to achieve the above and further objects, according to the present invention, there is provided an infusion pump system comprising at least
a pump adapted to be attached to a patient and to cause infusion of a drug into the patient's body,
a storing unit adapted to store at least a plurality of therapy data representing different therapies, a plurality of drug data representing different drugs, a plurality of protocol data representing different protocols each of which defines a specific drug delivery and/or application to a patient, a plurality of profile data representing different profiles relating to specificities relevant for a therapy, a plurality of care type data representing specific aspects of therapies, and a plurality of feedback data received from said pump and/or other sources and including information about particularities of therapies already carried out or currently running,
an input unit adapted to enable a selection of specific therapy data representing a specific therapy from said plurality of therapy data, specific drug data representing a specific drug from said plurality of drug data, specific profile data representing a specific profile from said plurality of profile data, and specific care type data from said plurality of care type data,
an associating unit adapted to provide an association of the selected specific therapy data, the selected specific drug data, the selected specific profile data and the selected specific care type data provided by said input unit and further adapted to determine on the basis of said association specific protocol data representing a specific protocol from said plurality of protocol data and specific feedback data representing a specific feedback from said plurality of feedback data, wherein said storing unit is further adapted to store said association along with said specific protocol data and said specific feedback data, and
an output unit adapted to output said specific protocol data along with said specific feedback data.

Accordingly, in the infusion pump system of the present invention, the storing unit which preferably can include at least one database stores a therapies list, a profile list, a drug list, a protocol list and a care type list as well as feedback data received from the pump and/or other sources and including information about particularities of therapies already carried out or current running. For the selected items "therapy"+"drug"+"profile"+"care type" (to be selected by the input unit) an association is made by the association unit so as to determine on the basis of this association a specific protocol and a specific feedback wherein the specific protocol and the specific feedback are the result and, hence, the output of a search in the storing unit. The aforementioned association and selection with eventual corrections are also stored in the storing unit. Finally, the output unit provides the aforementioned result as output, i.e. the specific protocol data along with the specific feedback data.

In accordance with the present invention, per each therapy the chosen feedback also called therapy feedback is provided so as to have a valuable tool to monitor the therapy outcome during the infusion which in particular may be last long for chronic patients, wherein at the same time it is allowed the use of a conventional drug library needed for present and future pumps to be used in a hospital for everyday's work. So, due to the present invention it is achieved to bridge the words of ambulatory infusion needs with hospital smart pumps and drug library.

A profile can relate to specificities for a therapy which gives different infusion protocols, wherein specificities can be e.g. patient attributes (like age), delivery route attributes (like intravenous or brachial block), and infusion rates (e.g. morphine infusion rates for a child and an adult are different).

A care type represents specific aspects of therapies and in particular can be defined as a particular therapy or a subcategory within a therapy like post-operative pain, palliative care, parenteral nutrition, post-operative pain regional, obstetric pain, chemotherapy, antibiotherapy, immunotherapy, primary pulmonary hypertension, concurrent infusions, sequential infusions, etc. and has a monitoring page to be output with feedback needs according to medical practice.

In the context of the present invention, it is mentioned that the term "drug" covers fluid pharmaceutical substances and other fluid therapeutic agents of all kinds.

Further, it is to be mentioned that in the infusion pump system according to the present invention not only one pump, but also a plurality of pumps can be used.

Preferably, said input unit is further adapted to enable input of updated feedback data for a given therapy, drug, profile and/or care type, and said storing unit is further adapted to replace current feedback data by said updated feedback data for said given therapy, drug, profile and/or care type and/or a current status of said pump. The status of the pump covers pump events of all kinds like "on", "off", "start-stop", "alarm", "infusion running", "rate", "volume infused", "time to end infusion", in case a plurality of pumps are used which of the pumps are logged in, etc.

In a further preferred embodiment, said output unit is further adapted to program said pump in accordance with said specific protocol data and to adjust the programming of the pump in accordance with said feedback data. This embodiment provides an essentially full automation of the system.

Preferably, said storing unit and said associating unit are included in a remote server, said input unit and said output unit are included in said pump, and said remote server is connected to said pump. In an alternative preferred embodiment, said storing unit, said input unit, said associating unit and said output unit are included in a remote server, and said remote server is connected to said pump.

Preferably, there is provided at least a terminal device connected to said output unit and having at least a display to indicate the output from said output unit. Alternatively or additionally, the terminal device can be connected to said pump and has a display to indicate operational data of said pump. The terminal device can be a personal computer or a notebook or a mobile device like a tablet computer or a mobile telephone.

In a further preferred embodiment, said input unit comprises a questions providing unit adapted to provide questions regarding the selected specific therapy and an answers providing unit adapted to provide answers to said questions as a feedback. According to a preferred modification of this embodiment, said questions providing unit is further adapted to provide one or several proposed answers of each question, and said answers providing unit is adapted to enable to select a proposed answer to a question as a feedback, wherein for instance, in case the specific care type data relate to a palliative care pain, the questions providing unit is adapted to provide at least a question of visual analog scale pains score at rest, or, in case the specific care type data relate to a post-operative pain, the questions providing unit is adapted to provide at least a question of visual analog scale pain score at rest and/or visual analog scale pain score at mobilization and/or numbness and/or motor blockage and/or satisfaction with regard to the specific patient. Preferably, the questions providing unit provides questions to the user who can be a doctor, a nurse or the patient.

In a further preferred embodiment, said storing unit is further adapted to store a plurality of nutrient type data representing different types of nutrient and a plurality of nutrient content data representing different contents of nutrient, wherein specific nutrient content data representing a specific content of nutrient from said plurality of nutrient content data for specific nutrient type data representing a specific type of nutrient from said plurality of nutrient type data are linked to specific therapy data representing a specific therapy from said plurality of therapy data and to specific drug data representing a specific drug from said plurality of drug data wherein a nutrient content is usually defined in kCal/ml (i.e. per volume unit).

According to a preferred modification of the aforementioned embodiment, said input unit is further adapted to enable an input of at least therapy data and drug data for storing in said storing unit, in case the specific care type data relate to an enteral or parenteral nutrition, said input unit is further adapted to enable an input of nutrient type data and nutrient content data for storing in said storing unit, and said output unit is further adapted to output specific nutrient content data, in particular per time unit, in accordance with the selected specific therapy and drug data. Accordingly, the input unit is not only adapted to enable a selection of specific items by the user, but also to be used by a doctor or a similar expert at setup of a therapy and an associated drug library. In case the input unit comprises the aforementioned questions providing unit, the questions providing unit is adapted to provide at least a question of nutrition content data for any nutrition type data when inputting therapy data and drug data. Further, for outputting in particular as a graph, during or after infusion, the specific nutrient content data should be preferably transferred from kCal per volume unit to kCal per time unit for displaying as a graph.

In a further preferred embodiment, said plurality of drug data includes data representing desired safety limits for a stored drug, in particular in accordance with specific protocol data. So, limits, preferably soft and hard limits, can be given in a drug library for the protocol data In a further preferred embodiment, said storing unit is further adapted to store a plurality of patient category data which differ from each other at least with regard of gender, age, bodyweight and disease severity, wherein, in accordance with specific therapy data representing a specific therapy from said plurality of therapy data and further in accordance with specific patient category data representing a specific patient category from said plurality of patient category data, specific protocol data representing one or more specific protocols from said plurality of protocol data are linked to specific profile data representing a specific profile from said plurality of profile data. In the light of the 5R rule (safety check prior to infusion: right patient & right drug & right protocol & right time to infuse & right delivery route), according to the present invention, three of the five items of the 5R rule, i.e. right drug & right protocol & right delivery route are stored in the drug library, whereas the remaining two items, i.e. right patient & right time to infuse are left for a care plan and infusion order time to associate.

Preferably, said output unit is further adapted to create a monitoring page defined by care type data and feedback data and adapted to be shown on a display. So, care type and feedback define a monitoring page specific to the feedback needs. The display can be provided at said output unit or at the aforementioned terminal device.

In a further preferred embodiment, said associating unit is further adapted to associate protocol data representing several different specific protocols to therapy data representing one or more specific therapies. So, multiple protocols can be associated to some therapies which in particular is useful for chronic patients at home using a few standard protocols.

In a further preferred embodiment, said storing unit is further adapted to store a plurality of care area data representing different care areas, said input unit is further adapted to enable a selection of specific care area data representing a specific care area from said plurality of care area data, and said associating unit is further adapted to additionally incorporate the selected specific care area data into said association. Care areas are specialized departments or portions of a hospital like intensive care unit, operational room or ward. Care areas in hospitals are mostly to be seen in correlation with a therapy, since mostly care areas are specialized and dedicated for a specific therapy so that care areas might be considered to be similar to therapies in the search or construction of a drug library. In a preferred modification of this embodiment, said associating unit is further adapted to associate protocol data representing specific concurrent and sequential protocols to therapy data representing one or more specific therapies, drug data representing one or more specific drugs and care area data representing one or more care areas. Accordingly, concurrent and sequential protocols can be linked to some therapies, drugs and care areas, wherein concurrent are protocols for many pumps carrying out infusion at one bed in particular in intensive care units or operating rooms and sequential are protocols that run one after the other like in chemotherapy or piggyback infusions.

In a further preferred embodiment, said storing unit is further adapted to store a plurality of alarm data representing different types and/or levels of an alarm, said associating unit is further adapted to determine on the basis of said association specific alarm data representing one or more specific alarms from said plurality of alarm data, and said output unit is further adapted to output said specific alarm data. According to a preferred modification of this embodiment, said plurality of alarm data include pump alarm data representing different pump related alarms. According to a still further preferred modification of this embodiment, said plurality of feedback data include occlusion alarm data received from said pump and indicating a temporary interrupt of operation of said pump, said plurality of alarm data include catheter blockage alarm data, said association unit is further adapted to determine said catheter blockage alarm data from said plurality of alarm data in case said specific feedback data includes a predetermined number of occlusion alarm data indicating a predetermined number of temporary interrupts of operation of said pump within a predetermined time period, and said output unit is further adapted to output said catheter blockage alarm data. In case there are a lot of occlusion alarms where the pump stops, then the pressure drops, and after an occlusion setup the pump restarts automatically and possibly after sometime occludes again, this is clinically an indication of catheter blockage.

The catheter blockage alarm data can be used not only as a warning about a current catheter blockage, but also for statistic purposes.

In a still further preferred embodiment, said storing unit is further adapted to store a plurality of feedback level data representing different levels for feedback data, and said associating unit is further adapted to determine on the basis of said association specific feedback level data representing a specific level from said plurality of feedback level data.

The present invention is solving the problem of medication error prevention also using a drug library but associated with means to improve the therapy through monitoring infusion therapy outcome and therapy adjustment. The former is more needed for mainstream infusions while the latter is needed in some longer term therapies like post-operative and palliative care analgesia, parenteral nutrition, immunotherapy, Parkinson's disease and others. The present invention is unifying the ambulatory and bedside infusion pump worlds that can potentially be served by a single pump and a backbone IT system.

Hospitals usually assign a therapy to a patient, starting at the hospital and at some point going external so that a home care provider continues therapy, and there is a need to share drug libraries and therapy feedback through networks. According to the present invention, assigned are health institutions such as hospitals, care areas within hospitals, and external home care providers, communicating through the same backbone IT system so that a hospital defined therapy and prescription is transferred with its limits and monitoring preferences to home care provider.

So, it is an aim of the present invention to provide an improved remote infusion therapy management system for interconnected devices as a further advancement of above prior art, serving both hospital and home care approaches, integrating drug libraries, protocol libraries, and therapy feedback parameters libraries, for safety ease of use and better therapy outcome. The present invention shall define alarms called therapy alarms that do not come from the pump itself, but from potential user health nuisance, discomfort or threats or a time in a therapy that needs protocol adjustment as for example response to high pain level, or accessories like catheters needing inspection to avoid complications. So the present invention provides means on the server to define such therapy feedback alarm levels and means to define therapy feedback qualitative or quantitative metrics. Further, it is an aim of present invention to provide multiple protocol management and monitoring different infusions combined, such as for drug volume monitoring facility so that in parenteral nutrition, hydration, and TPN or separate lipids and other nutrients are monitored in a timeline for therapy monitoring. Hydration and different nutrients are infused through a pump or different pumps at different times, but all patient related data concerning his intake can be shown on one display.

BRIEF DESCRIPTION OF THE DRAWINGS

FIGS. 3a to 3g show block diagrams in terms of somewhat like flow charts for illustrating the function of the system of FIG. 1; and FIGS. 4a to 4i illustrate examples of pages and windows to be shown on a display of a computer and/or a mobile device.

DESCRIPTION OF THE PREFERRED EMBODIMENT

Figure 1:
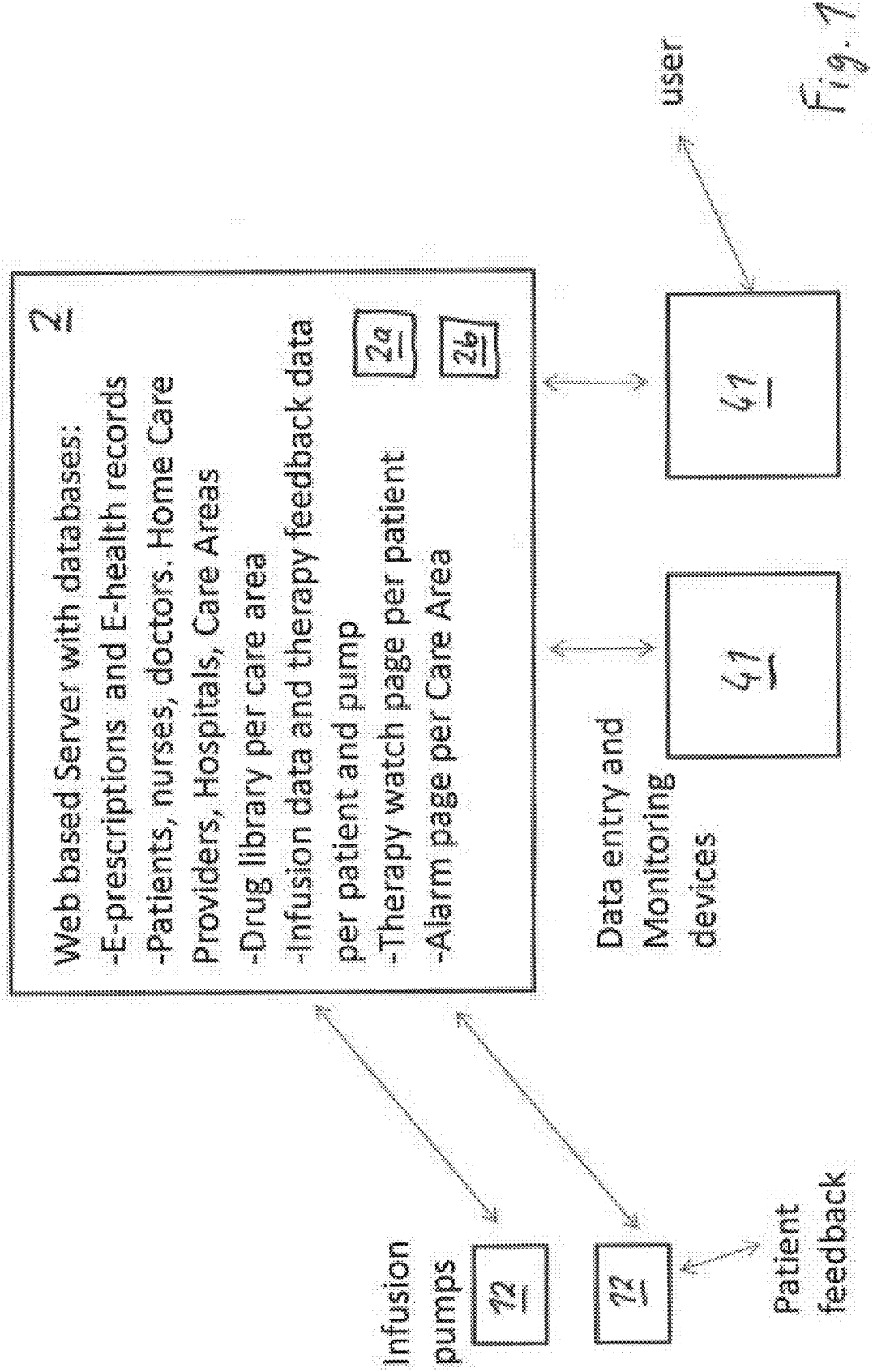
FIG. 1 shows a schematic block diagram depiction of an infusion pump system according to a preferred embodiment of the present invention.

An infusion pump system according to a preferred embodiment of the present invention is schematically shown as a block diagram depiction in FIG. 1 according to which the system comprises at least a remote server 2, infusion pumps 12 (both ambulatory and bedside), and terminal devices 41 which are provided for entry of data and for monitoring and, hence, commonly as an input unit and an output unit.

Figure 2:
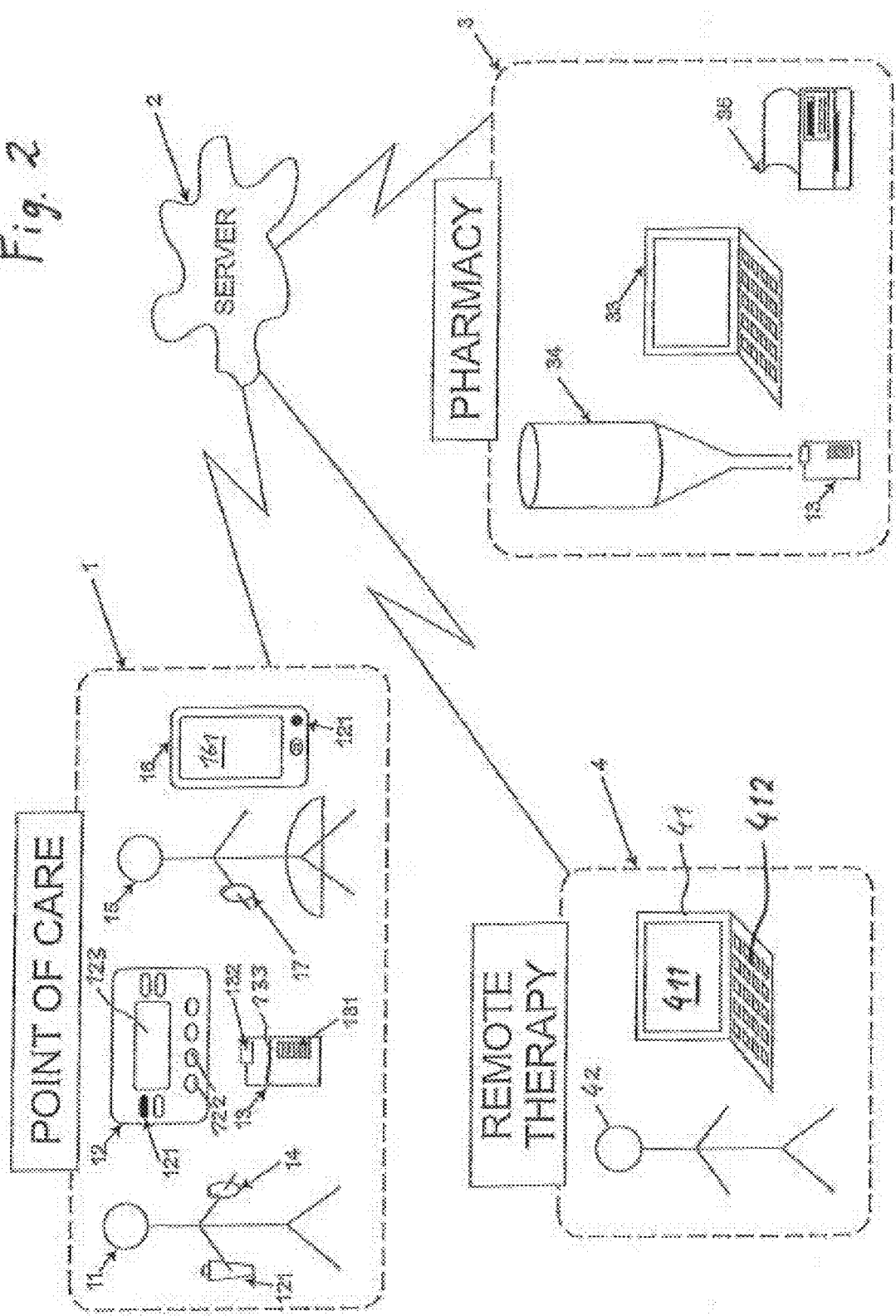
FIG. 2 schematically shows a block diagram depiction of some components of the system of FIG. 1 in greater detail.

In FIG. 2, the system of FIG. 1 is shown with some components in greater detail.

At a point of care 1 schematically shown are a patient 11, the pump 12, a drug bag 13, a nurse 15 and a communication device 16.

In the example shown, the patient 11 is provided with a RFID tag 14 which is attached to her/his body and preferably to her/his arm or finger as indicated in FIG. 2. Alternatively or additionally the patient 11 can also be provided with a "bolus" or "distress" button 121 which is attached to her/his body and preferably to her/his arm or finger as indicated in FIG. 2, too.

In the shown embodiment, the pump 12 is configured as a so-called miniature pump comprising all those features which are necessary for working as a pump and controlling the pumping function. So, the pump 12 includes a control means for controlling the pumping function so as to adjust the dose of drug(s) to be fed into the body of the patient 11 to which the pump 12 is to be attached.

Further, there is provided a questions providing unit (not shown) for providing questions regarding the effects of administration of the drug(s), and recording unit for recording answers to said questions. The questions providing unit and the recording unit can be included in the pump 12 and/or in the server 2.

As schematically shown in FIG. 2, the pump 12 is further provided with a "bolus" or "distress" button 121 and some further buttons 122 which are used for inputting answers to the questions after having been created by the questions providing unit. In the shown embodiment, the pump 12 further comprises a display screen 123 for displaying the questions as created by the questions providing means, the input answers and further data and messages. So, the questions providing unit, the display screen 123 and the button 222 can be considered an input unit or are at least parts of an input unit (which is not further shown). Moreover, the pump 12 includes wired or wireless bi-directional telecommunication means for being connected to other units and devices of the system.

In the shown embodiment, the drug bag 13 is provided with a label 131 preferably comprising a barcode and an RFID tag 132 and is filled with a drug 133. The drug bag 13 is coupled via a tube or hose (not shown) to the pump 12 so as to supply the pump 12 with a drug. Like the pump 12, the drug bag 13 is also adapted to be attached to the body of the patient 11.

Instead of being directly attached to the body of the patient 11, the pump 12 can alternatively be adapted to be attached to the drug bag 13, or according to a further preferred embodiment the pump 12 and the drug bag 13 can define a common unit to be attached to the body of the patient 11.

In the shown example, the nurse 15 is provided with a tag 17, too, which is preferably attached to her hand or finger as schematically shown in FIG. 2.

The hand-held mobile device 16 comprises a "bolus" or "distress" button 121, a large display screen 161 and can be embodied as a PDA (Personal Digital Assistant), a smart phone or a tablet personal computer having a telecommunication function. The screen 161 can be used as output unit for outputting all relevant data. In case the screen 161 is a touch screen, the screen 161 can also be used as an input unit, in particular for providing questions and answers to said questions. The telecommunication function comprises a short-range as well as a long-distance communication ability. So, according to the described embodiment the hand-held mobile device 16 includes a local area network interface for a wireless connection with a pump 12 via a local area network; however, rather than a wireless communication a wired connection between the pump 12 and the hand-held mobile device can be alternatively provided. Moreover, the hand-held mobile device 16 includes a long range network interface as well so as to communicate with external remote devices.

Remote from the point of care 1 is provided the server 2 which communicates with the point of care 1 via the internet. The server 2 includes at least one database for storing several data which are relevant for carrying out the several functions of the system as described later in detail. The data base which is provided as a storing unit is shown as a schematic block 2a in FIG. 1. Further, the server 2 includes an associating unit which is shown as an additional schematic block 2b in FIG. 1, wherein the function of the associating unit 2b is described later in greater detail.

Reference numeral "3" denotes a pharmacy which is schematically shown as a block in FIG. 2 and comprises inter alia a computer 33, a drug filling equipment 34 and a combined barcode label printer and RFID programmer 35 for printing out barcode labels and programming the RFID tag 132. The computer 33 includes a telecommunication interface for connection with the server 2 via the internet. The drug filling equipment 34 and the combined barcode label printer and RFID programmer 35 are coupled to the computer 33. The drug filling equipment 34 is provided for filling a drug bag 13 as schematically indicated in FIG. 2.

As further shown in FIG. 2, the server 2, is also connected via the internet to a point of remote therapy 4 where a computer 41 is located which is operated by a physician or doctor 42. The computer 41 also comprises a telecommunication interface for the connection with the server 2 as well as a screen 411 and a keyboard 412. The screen 411 is used as an output unit for outputting all relevant data, whereas the keyboard 412 is used as input unit for inputting inter alia and, if required, answers to the questions. Further, if required, the screen 411 can be used for providing questions and the keyboard 412 for inputting answers to the questions.

Further, in any unit of the system which unit is operated by a user, a user interface may be implemented as a hardware and/or software component. Preferably, the user interface consists of a visual program running on a display of such unit(s). In the embodiment according to FIG. 2, the pump 12, the hand-held mobile device 16 and the computers 33 and 41 include such a user interface as a visual program running on their display.

During operation of the system, questions are provided by the questions providing unit in the pump 12 and/or, if required, at the screen 161 of the mobile device 16 and/or at the screen 411 of the computer 41 which questions describe e.g. inter alia quantitatively and qualitatively the condition of mobility, pain etc. According to the kind of list or table of questions appearing, the user or patient may answer either "yes" or "no" or with a quantitative reference, e.g. by selection from a list of prescribed types of answers given as e.g. "bad"-"good"-"better"-"excellent" or numbers from "1" to "10". An example of the questions which may be different per used therapy and/or selected drug and of the kind of the corresponding answers is as follows:

| QUESTION | ANSWER |
| --- | --- |
| Pain VAS score | 0 to 10 |
| Pain during emotion | 0 to 10 |
| Extreme numbing | yes/no |
| Blockage of movement | yes/no |
| Difficulty in walking | 0 to 10 |
| Activity | 0 to 10 |
| Insomnia | 0 to 10 |
| Puffing of legations | yes/no |
| Satisfaction | 0 to 10 |
| Service assessment | 0 to 10 |
| Nausea | yes/moderate/no |
| Vomiting | yes/trend/no |
| Diarrhea | yes/slight/no |

The control unit of the pump 12 is adapted so as to adjust the dose of the pharmaceutical substances within predetermined limits according to the kind of therapy, pharmaceutical substance and/or user, which limits are preferably different between local and remote adjustment.

Additionally, sensors (not shown) can be attached to the body of the patient 11 which sensors are adapted to determine therapeutic results or side effects of the therapy due to the infusion of the pharmaceutical substances, wherein the controlling means is adapted to also adjust the dose of drugs in accordance with the output of the sensors. For instance, said sensors may be adapted to record convulsion and/or other measurable parameters of the user's or patient's condition. Moreover, implantation electrodes can be arranged near or on the relevant nerve(s) or epidermally and provided for quantitative controlling of muscle contraction. In particular, side effects can be identified by placing sensors in an implantable catheter tip as used in many chronic diseases in the blood stream (to read states such as temperature, blood pressure, glucose, oxygen and ions) or by the pump asking the user about conditions such as diarrhea, vomiting and nausea.

The questions providing means is adapted so that the frequency and timing of the questions is associated with the dosing of the pharmaceutical substances on the user's demand. So, the question frequency and their timing can be associated with the pressing of the button 121 at the pump 12 which button is provided as a distress button or dosing on demand (bolus) from the user or patient.

Additionally or alternatively, the questions may come at a predetermined time after an extra bolus administration or rate adjustment, and/or by means of an algorithm (preferably consisting of an artificial intelligence algorithm) determining the time after the aforementioned events (provision of the last questions, pressing the button, change of infusion rate or bolus).

The telecommunication means in the pump 12 and the hand-held mobile device 16 provide a communication between parts of the pump infusion system at the point of care 1 via a wireless low-power consumption network of a small-range or hard-wired network, and between the point of care 1, the server 2, the pharmacy 3 and the point of remote therapy 4 via a wireless long-distance network. The hand-held mobile device 16 is provided e.g. with a communication screen 161 where the questions can appear. In case of a touch screen, a "volume" gradient type graph can be inputted, too. Preferably, the wireless low-power consumption network has a BLE (Bluetooth Low Energy) function or any similar function for providing a low-range regional-personal network. In case of a long-distance mobile device, communication links using the TCP/IP protocol through WiFi, GSM/GPRS/UMTS, WiMax etc. are preferably provided.

The display of the mobile devices having a larger battery can be used as a remote display with the benefit of a larger size and color fidelity.

Preferably, the control means of the pump 12 is adapted to adjust the dose of the drug 133 (1.) by means of a programming to be performed locally or remote by the attending staff, or (2.) by means of a local or remote algorithm of an automatic control wherein the control means preferably includes neural networks and/or a PID (Proportional Integral Differential) algorithm resulting in a closed loop infusion control in both aforementioned cases (1.) and (2.). So, the correction of the parameters of the on-demand dosage and, thus, of the infusion can be done either locally at the pump 12 or via a local connection to the hand-held mobile device 16, or from remote. The pump 12 is programmed from the attending staff locally or from remote, or by means of an algorithm of dose correction by using a closed-loop system for providing a feedback. The automatic control system can include neural networks and/or PID algorithms wherein in case of a difference between a desired therapy result and a measured or reported current therapy result a corresponding error is generated by the algorithm. Preferably, for each on-demand dosage the volume of the drug(s) is algorithmically measured without a simultaneous change of the basal infusion rate. Should the automatic process correct the pump dosage, if a pharmaceutical company needs to keep the closed loop infusion control algorithm proprietary, the algorithm can be located in a server under its control and output to the pump through telecommunication or telemetry.

The server 2 includes at least one database 2a (FIG. 1) for storing data regarding therapy, administration of the pharmaceutical substances, configuration of therapy infusion system user interface for all devices, pharmaceutical substances per therapy, user questions per therapy, protocols and enabling options and limits for remote infusion adjustment per kind of therapy, alarm and alarm enabling configuration, safety check configuration, pharmaceutical substance, preparation description, infusion progress and events or actions, and means for transferring at least a part of said data to said control means, preferably along with at least one pass code, barcode, RFID and/or biometric recognition element. Preferably, the control means is adapted to allow the local and/or remote programming within predetermined limits according to the kind of therapy, drug 133 and/or user, which limits are preferably different between local and remote programming.

So, inter alia infusion protocols, events or actions of the pump(s) and sensors, the user's or patient's answers with the time of occurrence, further information of the users, physicians and other attending staff as well as therapies, drugs per therapy, usual and historic protocols per therapy and physician, safety limits for close or local and remote programming per protocol defining the therapy, drug, patient and route of communication can be stored in the database of the server.

The questions are initially stored in the server 2 after having been created, before the questions will be transferred along with infusion parameters to the pump 12. Then the questions will appear from the pump 12 to the user at the point of care 1, in particular to any local area network device, and can be changed from remote or locally via the connection with the present computer of the attending staff and a respective local monitoring program.

Protocol libraries are also included in the database 2a of the server 2 which is remote located and to be accessed via the internet. So, the protocol library and further contents of the database 2a can be easily shared between several institutions like e.g. different hospital divisions and home care providers. Moreover, one and the same pump 12 can be used for different treatments by using different protocol libraries or databases. For instance, such a pump can be used for anesthesia pain control on the one day and for parenteral nutrition on another day by downloading an adequate protocol list from the server 2. Further, a notion of patient centric programming can be introduced: If data regarding drug 133, concentration etc. are stored in the protocol of the database 2a, all what is needed at the pump 12 is to assign a patient by name or e.g. by an RFID or a barcode, and all are downloaded into the pump. Then, a nurse 15 just validates the right protocol, and the rest of the aforementioned safety rights are validated in the same manner so as to start infusion. As an example, the pump 12 can start infusion at a hospital and then stopped, so that all data are transferred to a home care provider who can come with another pump download data and continues infusion at home. Namely, usually a therapy starts in the hospital by using a hospital pump and continues at home by using a pump which is provided from a home care provider. For such a procedure, the relevant data about the infusion and the infusion status like volume infused or to be infused, lockout time for bolus etc. along with the protocol in use and safety options are uploaded from the hospital to the server 2 and downloaded from the server 2 to the pump of the home care provider for continuation of infusion in particular by using the same drug bag 13.

Preferably, the server 2 can comprise an array of interconnected computers (not shown) each of which includes the part of the database which is under the competence of the responsible attending staff or office. For instance, the pump 12 and the associated database (including inter alia medical histories and protocols) can be managed and the corresponding data can be stored in a server 2 located with a vendor or sales representative in the respective country, in the patients' databases with their medical histories for a treatment being stored therein, and/or in databases of hospitals and/or home care companies to be accessed by physicians, nurses and other attending staff. Such data are retrieved by a user interface, which is installed in the server 2. Since the communication is carried out between medical devices, the use of the international standard protocol "HL-7" is preferred. Composed are the data for communication with the patient 11 by means of known communication techniques, e.g. via webpages, smart phone, tablet personal computer, PDA (Personal Digital Assistant) applications etc., or with the pump 12. The stages of the therapy, such as prescription, sending to the pharmacy the pharmaceutical substance(s) to be packaged etc., can be part of the pump infusion system or be provided by application of another system with which there is a communication. Respectively, alarms from the pump 12 or occurred during the therapy (in particular through feedback from the sensor 2) can be forwarded to a hospital alarm server provided in the hospital or the home care or rescue company (not shown).

Server web pages can be used by the hospital service or a home-care provider and include data about patients treated and nurse personnel organized in groups. So, the nurse 15 who is in charge of the patient 11 will receive via telecommunication a message (in particular an SMS) describing a problem encountered with the pump 12 or the treatment, or be informed that in a given time the drug reservoir must be replaced. From a list of patients, the attending staff can watch the infusion (events and graphs) and therapy progress of each patient in real time over the internet, with alarms popping up in such list.

Further, a patient monitoring service (not shown) can use and access the database, e.g. via the internet, in order to reveal e.g. the dose infusion history and the answers to the questions. Images, in particular including graphs, can be generated and depicted either locally or at the pump 12, the hand-held mobile device 16 or the large distance mobile device or at a local or regional computer or tablet personal computer by using a local connection. In particular, the data of the pump 12 automatically appear on a computer (like e.g. the computer 41 at the point of remote therapy 4) or a tablet personal computer (like e.g. the mobile device 16 at the point of care 1) of the physician, nurse and/or other attending staff, which enters the local network connected with the pump infusion system with a password exchange according to the safe network practice, and can be stored on the computer for further processing (e.g. data logging). In case the pump 12 is not connected to the server 2 and a hand-held mobile device 16 of a nurse 15, which is connected to the server 2 online, passes by the not connected pump 12, a connection between the pump 12 and the hand-held mobile device 16 can be automatically established through the local wireless network so that data will be immediately exchanged between the pump 12 and the server 2 via the hand-held mobile device 16.

Security is ensured with the ascertainment of both the digital signatures of the participants of the communication who usually are patients on the one hand and physicians or nurses on the other hand, as well as by using a full cycle of information. In the embodiment shown in FIG. 2, the digital signatures are included in the output signals from the tags which preferably consist of RFID tags 14, 17 and 132 shown in FIG. 2. As already mentioned above, one of these tags, i.e. the tag 132 is provided on the drug bag 13 adjacent to label 131 which partially or completely indicates data like therapy, patient, pharmaceutical substance used, infusion parameters and infusion limits, while the same data are also stored in the RFID. The reading-out from the system or from an accessory of the nurse 15, the transfers to the pump 12 and the system and also the identification is carried out, if it is the right patient 11 who receives the correct medication and infusion protocol regarding the correct disease within the limits allowed, and the correct administration route, and following the identification the pump 12 is possibly programmed accordingly, and the infusion to the patient 11 is allowed. The mentioned accessory of the nurse 15 can be a tablet personal computer or an RFID reader which can be automatically or manually connected to the local network of the pump infusion system.

During the therapy or infusion, by pressing the distress button 121 or arising a sensor alarm, questions are sent to the patient and then the answers are received, and according to said answers a correction of the infusion is carried out by means of an automatic control or by a remote action of the physician 42 at the point of remote therapy 4. Following a successful identification of the physician 42, a safe remote programming is carried out within limits, so that in such a case the physician 42 also works as a programmer.

Preferably, the user's or patient's safety is increased by limiting the range or amount of alteration of the initial parameters so as to allow the pump 12 to be additionally programmed within limits only. These limits are initially provided by the pump 12 and transferred to the server 2 and from the server 2 to the user interface, so that the patient 11 is prevented from programming outside the limits. These limits include lower limits above which the programmer is informed in order to avoid errors. Further, the limits can be extended in therapies such as regional analgesia, where the risk is lower, or narrowed in case of intravenous or epidural analgesia or other diseases where the risk is greater. These limits can be set up by the pump if it is programmed preferably by a so-called "therapy" menu, or by a physician (using a maximum permissions programming code) if the pump 12 does not have any programming regarding therapy and/or drug 133. So, due to these safety limits implemented in the pump, the infusion is limited in case of an internet malfunction, wherein these limits are different for different therapies, drugs and/or patients. The responsible attending staff (physicians or nurses) has to validate on the pump 12 the limits received from the server 2, before remote programming is allowed. The initial therapy protocol and the limits for the therapy, i.e. the limits of alterations permitted by the protocol, can be programmed by any means, e.g. manually at the pump 12, at the hand-held mobile device 16 or by downloading through the internet, wherein validation of the attending staff on the display screen 123 of the pump 12 or on the display screen 161 of the hand-held mobile device 16 controlled by the pump 12 is required through the aforementioned safe process. The remote programming, in particular for correction of the current therapy, which e.g. is carried out by the physician 42 on the computer 41 at the point of remote therapy 4, is allowed with the aforementioned process only within the validated limits.

So, the pump 12 is preferably provided with the ability to let the attending staff, the automatic pump process or the distant server 2 change certain infusion parameters within a predefined limit. These parameters can also be changed by the physician over the internet by using a safe telecommunication or telemetry process as discussed below (in particular cf. lines 13 to 15 of page 23). The method used by medical personnel is the automatic process of 'trimming within limits' preset by the physician. The pump 12 is able to observe these limits so as to prevent excessive over- or under-infusion.

The data regarding therapies, drugs per therapy, protocols and safety limits of local and remote programming per therapy/drug/type of patient can be, preferably gradually, downloaded from the server 2 to the pump 12 for manageability purposes, preferably with fewer choices, as many as the use of the pump requires, and for the maintenance of a database updated with the latest data.

Although some functions of the system as shown in the FIGS. 1 and 2 have already been described above, in the following the complete functionality and operation of the system will be explained with supplementary reference to the FIGS. 3a to 3g.

The server 2, which can be in the cloud and via an IP address accessible for all terminals like pumps and other interoperable IT systems, incorporates and partially shares with pumps a number of databases and generates a number of infusion and therapy monitor and interaction pages for distant users of mobile or stationary computing systems. The total system can carry out infusion related IT tasks as conventionally done with infusion pumps or other hospital IT systems.

Smart pumps as described in US 2016/0051750A1 or EP 2 987 517 A1 can be paired preferably through RFID or NFC connections with mobile devices such as tablets or phones on which specific applications or simple browser are running and programmed by them easier, since they have a large display and touch keyboards and can follow quick technology changes in the IT field while pumps must be used for a long time with difficult regulatory wise changes. In case these devices and the server are class IIB or III certified, there is no need of validation on the pump, or the protocol has to be validated otherwise. The pairing procedure can be done by approaching the mobile devices to a pump so as to see the available pump serial number (S/N) and ask for an RFID/NFC reading and pairing process or read their barcode serial number (S/N) or through WiFi signal strength sniffing (cf. US 2015/0151051 A1 or EP 2 881 875 A1) of both the pump and the mobile device, so that in case of similar antenna signal strengths i.e. a geolocation pattern is found by the server to show pumps in vicinity available to be paired with.

The pumps 12 of the system also have RFID/NFC and barcode readers (not shown) integrated so that they can directly scan a patient's bracelet or face photo and medication.

But such task can also be done by a suitable app in the computer devices 16 and 41, and the information is then sent to the server and associated to the pump paired with the device. Medication safety is assured if the pump 12 and the drug bag or medication reservoir 13 are connected with a short upstream tubing or without the provision of any upstream tubing, and barcodes of both the pump and the medication are read in a short time sequence.

The server 2 through its continuously updated drug library associates a drug name, concentration and expiry date to a barcode identification (ID) number, or the pump can do the same by download from a drug library which is updated regularly by the server 2. In case of providing an RFID on the reservoir, a 100% safety is assured as described in US 2016/0051750 A1 or EP 2 987 517 A1.

The scanned patient ID or facial photo (from pump or mobile device) enables to give from a patients' database (interoperability with hospital IT systems) provided in the server 2 his name, age and weight or body surface area (BSA) that are sent back to the pump and app/browser.

So, with a procedure of pump itself scanning patient and medication or scanning from an app and pairing with one or more pumps, and with the server and pump databases interpreting IDs to names and data, an app and pump show the name of a patient, who will receive infusion, his therapy and feedback specification as described below, age qualifier, weight and BSA for dose calculation, medication name, concentration to calculate dose in mg/Kg/min, expiry date to avoid wrong administration, delivery route, delivery time, and protocol if available in the database (interoperability with hospital IT systems) and not programmed on site through the mobile device or pump itself. A complete procedure according to the 5R rule (right patient, right drug, right dosing, right application, right time) is facilitated by the connected system according to the described embodiment. The app preferably does not have a programming menu itself, but receives programming pages from the server. The encrypted security is SSL assured both from the pump and apps, and furthermore data are exchanged with a methodology explained in U.S. Pat. No. 8,551,038 B2 or EP 2 410 448 A1, wherein data go from a first location (one computer or pump) to a second location (another computer or pump) and reflection data are sent back to the first location after logging and reading log, then compared to initial data at the first location and sending an identical confirmation to the second location. This results in a higher security than a simple CRC and single transmission as explained in above prior art.

Conventional smart infusion pumps use so called drug libraries to reduce medication errors defining limits of infusion parameters per drug and patient or therapy characteristics. Categorization helps a database search to reduce drugs or infusion profiles from a big list to a manageable one and to associate patient characteristics for a given therapy to a correct infusion profile.

So, a drug library and its search categorization has the form of Therapy or Care Area>Drug>Qualifier or Profile (age, weight, therapy severity, infusion site, infusion specificity) and the output of the drug library search gives limits of protocol parameters for programming and eventual titration or reprogramming. These limits are soft if they can be overrun after simple warning, or hard if they cannot.

The present invention as inventive step associates the above categorization "Therapy or Care Area>Drug>Qualifier or Profile" with an on-screen remote monitoring per therapy so as to display therapy specific feedback means for therapy monitoring. This is done by the associating unit 2b integrated in the server 2 as schematically shown in FIG. 1. So, it is more a therapy telemedicine system than a classic drug library, very useful in home care settings where the patient is far from his caregiver. The drug library can be accessed also with a drug ID number just scanned from a barcode or RFID to retrieve drug name and all related safety data and eventually therapies to be used for as a reverse way to read the drug library database. It provides drug compliance information to medical personnel, regarding quantity infused, infusion time (displayed as a graph), delivery route, drug type and therapy feedback like bolus button press, sensor feedback and answer to questions.

So, the drug library database structure comprises links between:

Medication ID No. as read on barcode—Drug Name-Concentration-Expiry Date-Therapy-Therapy Feedback means-Patient Qualifier or Profile (age, BSA, weight, severity of illness, infusion site, infusion specificity). It needs scanning of both patient and drug data to work, or patient data are input by a user if needed.

A drug incompatibilities database checks multiple concurrent infusions for allowance. Some drugs should not be infused at same time with others; this knowledge is put in said specific database to check concurrent protocols.

The connected pumps 12 according to the present application send data to a server as therapy feedback, as programmed with the above association of therapy specifiers, i.e. output per query of the new advanced drug library according to the present invention.

For example, in parenteral nutrition:
In the drug library there is a selection
Care Area=Parenteral Nutrition and associated therapy monitoring Parenteral Nutrition
Drug=TPN
Profile=adult Associated with the patient's name, there is a protocol for each category of his nutrition, total parenteral nutrition (TPN), hydration, etc. taken in different days months or years and pressure of its catheter to identify possible implantable catheter obstruction. All this is a valuable therapy feedback to the therapist, collected from the server and pump, placed in a database in association with the patient's name and pump history.

In "Parenteral Nutrition" therapy monitoring page as programmed in accordance with scenario 2 as described at the end of the specification (cf. page 44) and to be displayed e.g. on the screen 411 of the computer 41 (wherein such a screen has the function of an output unit) for this patient, it is shown a historic infusion rate per nutrition type over more than one infusion, even more than a year where in most cases the patient is a chronic patient, a downstream pump pressure graph together with an infusion graph versus time and warnings if pressure has some characteristics that may cause catheter blockage, all drug volumes and nutrient content, i.e. hydration or TPN, or other, weight graph (from a connected weight scale) and a kCal/time per nutrient graph so that the doctor can on one page have all relevant information over all the time, wherein all infusions are sequenced on a time graph, to conduct therapy management of the patient.

On a "Palliative Care Analgesia" therapy monitoring page to be displayed e.g. on the screen 411 of the computer 41 (wherein such a screen has the function of an output unit), associated to palliative care therapy drug library query, a VAS pain scale of a patient is shown and pain levels above a limit (from the drug library) have different color so to alarm for therapy adjustment. The infusion pump is asking a pain scale question on the pump, and the corresponding answer is reported to the server. An infusion graph and bolus given over it and statistics of % of bolus asked divided by bolus given are displayed on a patient's therapy page provided by the server 2.

On a "Post-Operative Analgesia" therapy page as programmed according to scenario 1 described at the end of the specification (cf. page 43) and to be displayed e.g. on the screen 411 of the computer 41 (wherein such a screen has the function of an output unit), several questions for motor blockage etc. are shown with the answers from the patient on the infusion pump, so that the doctor can increase or reduce analgesia depending on motor block age behavior. An infusion graph and bolus given over it are displayed.

On a "Chemotherapy" page to be displayed e.g. on the screen 411 of the computer 41 (wherein such a screen has the function of an output unit), it is shown drugs and drug sequence as delivered, and also answers to questions such as "vomiting" and other side effects.

On a "Parkinson's" therapy page to be displayed e.g. on the screen 411 of the computer 41 (wherein such a screen has the function of an output unit), patient kinetic sensors (accelerometers) report tremor, normal or Levodopa Induced Dyskinesia LID, or Bradykinesia, and also specific kinetic tests, so that the doctor can adjust therapy. In such case, all kinetic artificial intelligence logic is based on the server which analyses raw data from sensors transmitted through the internet.

On a "Diabetes" page to be displayed e.g. on the screen 411 of the computer 41 (wherein such a screen has the function of an output unit), infusion rate and bolus are displayed versus time at one level, and glucose monitoring is displayed in another level.

A therapist's monitoring page to be displayed e.g. on the screen 411 of the computer 41 (wherein such a screen has the function of an output unit) may have a list of his patients, their therapy and pump serial number(s) (SN), and pending alarm from the pump itself indicating low battery or near end reservoir, or from the server through collected feedback questions or qualitative analysis of data according to an alarm rule put on the therapy specification page. So, an alarm is characterized by a color for immediate attention like a stop of infusion or other color for pre-alarm like a pain level of patient above a limit. The alarm can be acknowledged by the doctor so that it exits from the alarm list. The server can send a text message to the medical personnel in charge of the patient (like home care nurse) with alarm, so that a therapy correction is done as soon as possible. The alarm can be also sent to be displayed on interoperable hospital alarm monitors. The alarms are displayed on the patient's therapy monitoring page and patient alarm list. Alarms can be issued when a determined threshold is reached, but also from statistical evaluation of data, for example as how many times a threshold has been reached in a time period. So a pre-alarm can become an alarm from its frequency of occurrence or other more complex statistical evaluation of data in the database.

Furthermore, in view of a therapy feedback, since the system monitoring has pumps and monitors interoperable, the drug library can have a field for third party alarm actions. In case the patient is having low blood pressure or bradycardia or tachycardia or stop, for a given drug, the pump can run an alarm protocol for the alarm type and drug being infused, so that by means of pre-configured actions in the drug library a pump does a robotic infusion preventing that an anesthesiologist in panic may not act correctly and with best speed for so many pumps infusing. These death preventing actions may be discussed and decided as best practices by the doctors and put in the drug library feedback section and alarm case robotic infusion protocol downloaded into the pump upfront together with normal infusion protocol.

On a patient's therapy watch page to be displayed e.g. on the screen 411 of the computer 41 (wherein such a screen has the function of an output unit) it is also shown the location of the pump and, hence, of the patient (very useful in pediatric clinics where kids run everywhere), but also at alarm list page the location is displayed aside. The location is determined by WiFi alone or WiFi and GSM signal strengths recording and assignment of a location to a bundle of strengths and antennas, and preferably displayed on Google maps as disclosed in US 201570151051 A1 or EP 2 881 875 A1.

In many times, an infusion is initiated at a hospital, and then the therapy continued with several infusions by a home care provider. According to the present invention it is specified which home care provider from a list is going to care a patient after leaving the hospital so that there remains access of the hospital drug library section limited for the patient, thus resulting in having the same error prevention in therapy continuation. There are no rights to write into the drug library, but there are only rights to use contents for the common patient.

The service is accessible to terminals like the computer 41 at the point of remote therapy 4 via internet basically by means of a cloud service for both setup and monitoring, while all pumps are connecting to the same server to a socket with TCP/IP protocol. Pumps are storing historic and user feedback (answers to questions) data internally as long a connection is interrupted and sends them when connection is restored. Normally pumps send status information every 5 minutes or so and alarm information immediately on the event. So, the server 2 reflects the actual infusion status and patient feedback through devices as a bolus button or a measuring device such as glucose meter, or answers to questions on said therapy watch page. Connection is done using GSM/GPRS data connection or WiFi networks. This is an Internet of Things (IoT) system and a cloud service of its own. Server/data centers can be located in one or more locations. The server 2 stores received information and doctor actions (like acknowledgments or therapy correction as infusion rate and protocol change) in a number of databases (one of which is exemplarily shown as block 2a in FIG. 1). The server 2 may have in a database a local Medical Electronic Health Record (MEHR) of patient and Electronic Prescription (EP), while the system is interoperable with other MEHR and EP systems.

In U.S. Pat. No. 8,551,038 B2 or EP 1 385 420 B1 and US 2016/0051750 A1 or EP 2 987 517 A1 it is described a pharmacy automation so that a drug and also a patient are detected from the infusion pump as well as download protocols and limits and eventually alarm protocols according to the drug library association as described above. Therefore a complete drug library download onto a pump is not needed for a connected pump since more and more speeds and connectivity issues are getting better. This patient centric programming greatly eases programming, since a pump can detect a patient and a drug from smart labels and download all pending protocols and infusion in accordance with the 5R rule (right patient, right drug, right dosing, right application, right time), so that a nurse executes the one relevant for the time of infusion. The programming can be performed on the pump itself or on a mobile application. A program validation by a nurse on the pump is needed as long as the server and communication are not fulfilling standards for class IIB or C medical device safety. In the prior art, programming starts with annoying questions like "Continue last infusion?" or what type of therapy or what kind of protocol, what drug, etc. The present invention simplifies the programming menu by guiding the user according to scans or communications. For example scan patient's ID with a handheld miniature pump (cf. US 2016/0051750 A1 or EP 2 987 517 A1), then pump sends patient ID to the server and gets back a prescription including a programming protocol. Then, the user scans the medication reservoir, and the pump checks if identical to prescription to allow infusion (5R check). If no prescription available, the app or pump are guided to a new drug menu, and from the patient's therapy data received from the server the therapy menu pump gets the location by means of WiFi signal strengths scan (cf. US 2015/0151051 A1 or EP 2 881 875 A1), the correct drug and the protocol library to use. Communication is server centric, both pump and application communicate with server and not between them directly.

If there is no scan of the drug and if a previous infusion did not get an End Of Infusion alarm, then the pump asks if the user wants to continue the last infusion.

A protocol library is partially in every pump and in a larger extent in the server. Protocol libraries are categorized also by therapy or care area and drugs to be infused. There are protocols that are written as such for a care area, and others that include accumulated experience from many infusion histories. A user can use the one or other option to avoid full manual programming. Especially for multiple pumps on the same patient as usually used in operating rooms, parallel infusions and therefore multiple programming are the case, or in cancer protocols sequential infusions from one or more pumps are the case. According to the present invention, shown protocols are associated to a user with therapy, the user and his preferences himself, the care area and preferences (protocol type if not simple one) and a quantifier of a 3 dimensional description, with protocols in z axis, parallel infusion protocols spread in y axis and sequential protocols in x axis. So, since all pumps can read their associated reservoir through RFID or barcode, the mobile app facilitating programming reads from the server drugs—concentration-exp. date-concurrent or sequential infusion plus all rest of 5R. Only protocols having most of the drugs read are proposed to ease programming as an inventive step over prior art (U.S. Pat. No. 8,894,631 B2, WO 2016/196098, U.S. Pat. No. 8,172,798 B2). So, sequential drug infusion can be done by several connected pumps or by one pump and several valves (cf. US 2016/0051750 A1 or EP 2 987 517 A1), or all drugs are infused by the same pump one after the other where the system starts the infusion of the next drug automatically when the previous one is ended. Pumps in parallel are normal miniature pumps with full functionality as standalone (as in the above prior art) connected on a rack so that the system knows they are functionally connected in parallel or sequence for the same shared patient data that are scanned only once from any system pump. Another option described in the above prior art is to use pumps without display and battery that have RFID/barcode integrated and a cable connected to a monitor display multiple infusions controller.

Further particularities of this preferred embodiment are described as follows.

Therapies, care areas and drug lists are provided. Further provided is a creation of organization defined therapy categories and care areas (cf. FIG. 3a) (later: therapy categories can be assigned with care properties). Care areas are mostly used in the prior art for hospital use, but for home care therapies and therapy categories are more relevant to define a drug and a treatment. A creation of the organization structure is done by defining units, rooms, beds. For each room and/or bed the signature of the WiFi signals (level and mac address received from access points) can be associated. The units can be associated with the defined care areas.

Further provided is a creation and management of an organization drug list (drug name, concentration, reference code) and an association of parenteral and enteral nutritional fluids with nutrient content in the drug list (later: is utilized in the presentation of infusion data per nutrient content).

Methods and rules related to patient binding (e.g. allow patient association through the pump via a patient list nearby the pump on the pump display or barcode scan), 5R verification process (e.g. drug verification by barcode or RFID scan), operator auditing and security (e.g. require barcode or RFID scan of operator or user PIN), device programming (e.g. enable auto-programming or second nurse verification) and care plan termination can be defined per care area or therapy. Optionally patient's weight and/or BSA (body surface area used often in oncology drugs) is downloaded from server for dose programming (mg/kg/min) used in hospitals.

Figure 3A:
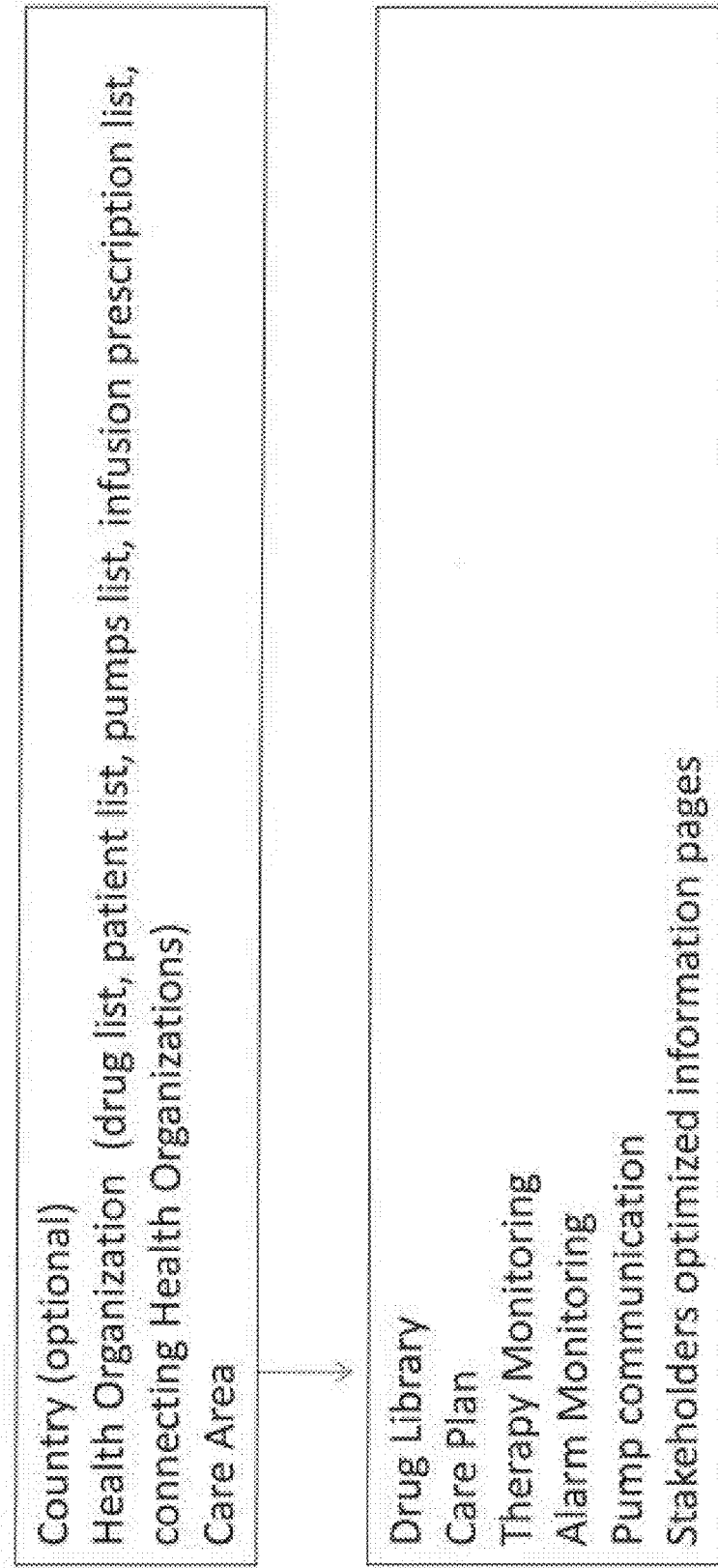
Figure 3B:
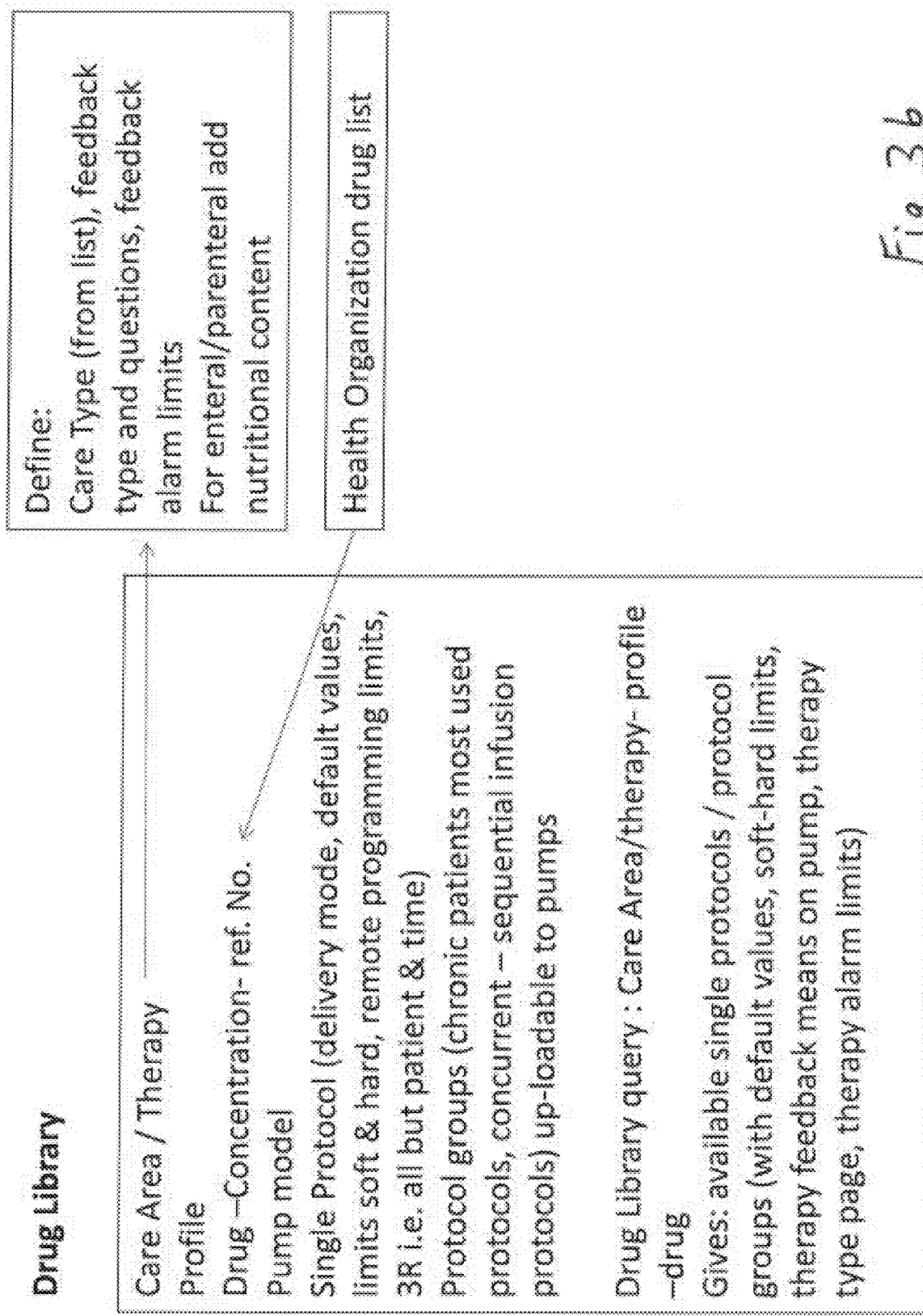
Figure 3C:
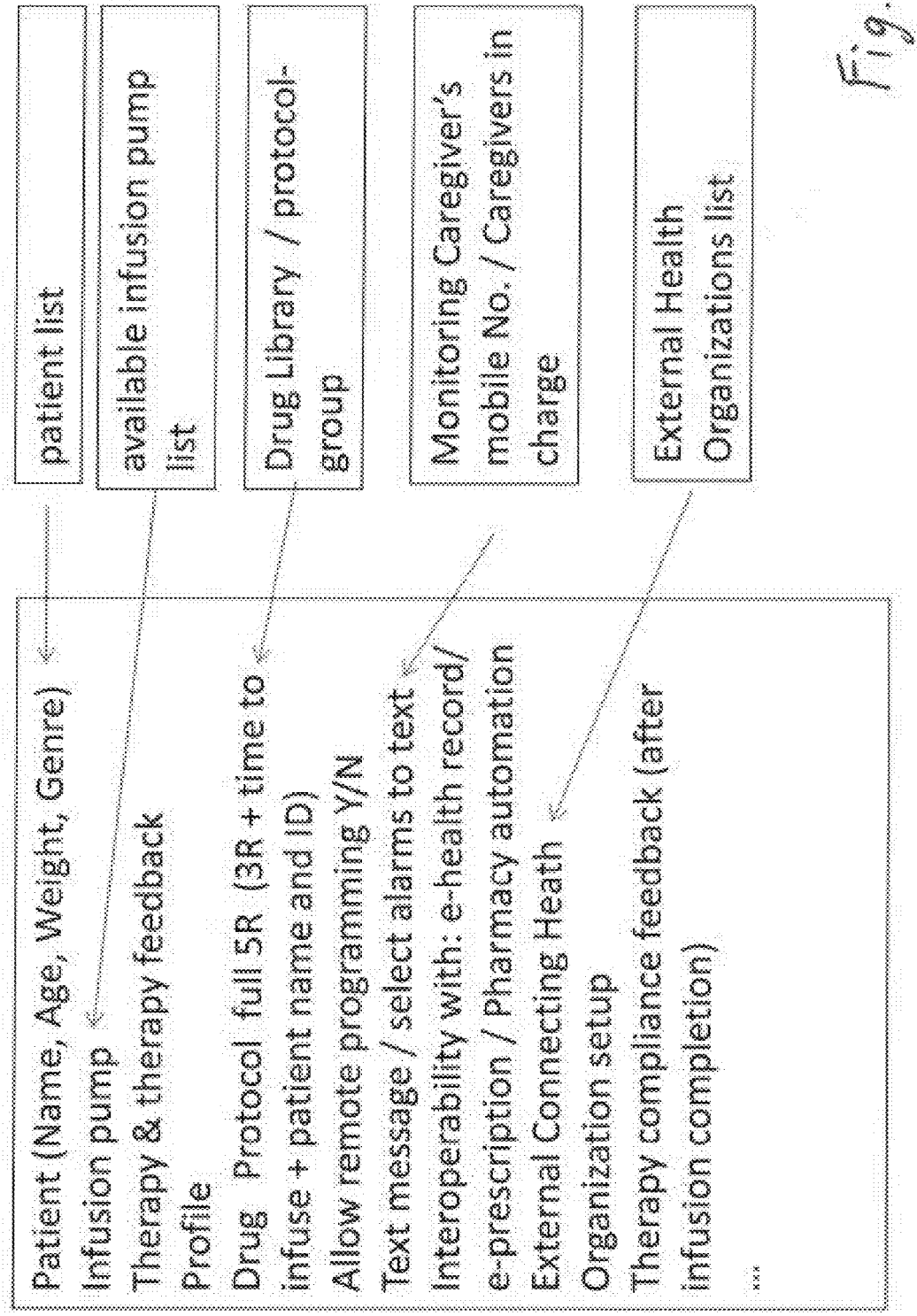

Delivery protocols can be defined and organized in a drug library or protocol library structure (cf. FIG. 3b). Delivery protocols (beside the default delivery settings, device settings, programming safety limits which is known in the state of the art) may include enable/disable of remote titration, how clinical observations can affect the delivery automatically (e.g. high CO2 stops morphine delivery), or in case of critical medication special rules for programming and verification like requiring an additional confirmation from a second clinician on the pump Each care area or therapy can be associated with a subset of the drugs in the organization drug list as well as with one or more specialization criteria called profiles.

Each combination of (1.) care area (like ICU or cancer ward) or therapy (like pain) or therapy category (like post-op pain regional), (2.) drug, (3.) patient profile (categorization like child or adult, or type of treatment like sciatic nerve block), and (4.) pump model can be associated with one or more delivery protocols and titration limits.

Care areas can optionally reference one or more therapies.

Device settings (e.g. alarm settings) can be defined per care area or therapy (and optionally per profile or drug if required).

Multiple care areas and/or therapies can be grouped so as to create pump drug library files that include all the parameters defined in the system per care area or therapy. If a care area has been associated with a therapy, all information for this therapy will be included and, hence, presented. Pump drug library files can be downloaded wirelessly or though wired connection to the pumps.

The system interface for browsing protocols in the drug library depends on whether the first index criterion is "care area" or "profile".
case 1: Therapy>Profile>Drug
case 2a: Care area>Drug>Profile
case 2b: Care area>Therapy>Profile>Drug A drug library fulfills only three items of the 5R rule, i.e. right drug & right protocol & right delivery route as a result of a query as given above.

In an ambulatory care, the specialization of the therapy is frequently needed. In contrast, in a bedside care use scenario, the care area is rarely required to be specialized. However, in a bedside use scenario, there could be a need for differentiation of the delivery protocols for specific drugs and the profile selection after drug has been selected in accordance with answers to this need.

In specific ambulatory therapies like parenteral nutrition, the patient may be prescribed with different medications or fluids. In these cases, the caregiver or the patient may have to switch between few delivery protocols. In this case, a simpler mechanism than the drug library is provided.

For the above cases, in a protocol library, simple ordered lists of delivery protocols (protocol groups) can be created, containing one or more delivery protocols for specific patient categories (cf. FIG. 3b). The protocol groups can be optionally associated with a therapy. For hospital use, protocol groups are associated with concurrent protocols, i.e. protocols to easily program a multiple pump stack that are to run concurrently like in operating rooms and ICU, or sequentially for several medications to be delivered one after the other like in chemotherapy or piggyback infusions.

Delivery protocols can be associated with a drug from the organization drug list, and a display name can be associated with each protocol.

The protocol displayed name could be more user friendly, easy to memorize a name for the patient, simpler than the drug or fluid name (e.g. "Dark yellow" instead of "Dextrose25%+Vitamins").

Device settings (e.g. alarm settings) can be defined per protocol group.

Protocol group pump files can be created for each protocol group and downloaded wirelessly or through wired connection to the pumps.

The system interface for browsing protocols in a protocol group is simpler compared with the drug library, since it is a simple list of names associated with each delivery protocol. In case a modification is allowed and performed on the pump for a given delivery protocol of the protocol group, this change persists on the delivery protocol data.

Protocol groups are created for concurrent infusions (multiple pumps at the same time) or sequential infusions (many drugs through a single pump one after the other such as those encountered in chemotherapy) to ease programming of the pumps.

Care properties predefined in the system are associated with feedback mechanisms (like as clinical questionnaires or vital signs monitoring devices).

Predefined or custom questionnaires as feedback mechanism can be associated with feedback properties that define the triggering mechanism (like trigger time interval or triggering events) and the system interface that will appear on a screen. Triggering mechanism can be fixed or adaptive based on the answers given. The creation of questionnaires, defines questionnaires as an ordered list of questions (customized or predefined) or adaptive flow of questions based on the answers given with scale i.e. when an alarm is triggered and a list of available triggers as for example bolus request, new infusion, scheduled times during infusion etc. Questions can have different format (numeric, ordinal multiple-choice, multiple-choice, free text and the answers are associated with clinical observation code) and could be mandatory or not.

Predefined or custom questionnaires are associated with therapy categories or care areas.

Therapy questionnaires configured to appear on the pump user interface can be included in the drug library or protocol group pump files and uploaded to the pump or as will be explained below Alarms are generated by a server subsystem. Observations from questionnaires or devices can be linked with alarm means characterized by one of the alarm condition, alarm priority, alarm model (latching, non-latching, time point event, start only, start-end) further grouped per therapy categories or care areas. A smart alarm system is generated by a Systems Alarm Rule page, configurable per therapy category or care area and evaluates data of the care plan, optionally compares them with data from other similar care plans and generates alarms accordingly. Pump questionnaires are included in the drug library or defined and edited per patient and uploaded for each patient.

Figure 3E:
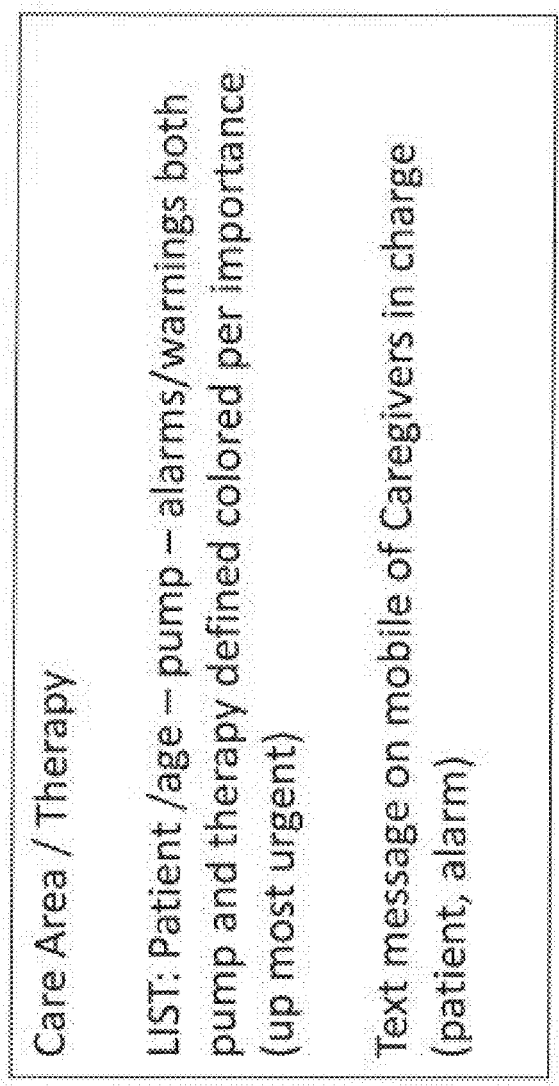

Rules per user type and end point type (email, SMS Text message, build-in notification system) for disseminating alarms and notifications generated by the system (devices and server) (cf. FIG. 3e). SMS and email notification for alarms may not include patient identification information according to the patient data protection legislation, but could include a deep link that leads to the specific patient and care plan views of the system that is related to the specific alarm.

Each user can assign himself as "in charge" of the organization or of a specific user group in order to receive the SMS and/or email notifications. Each group can be associated with specific care areas, therapies and/or care plans so that its members receive only alarms and notifications from these care areas, therapies and/or care plans.

Alarms can be transmitted to HIT systems. Interoperability example based on integrated health care enterprise alarm communication management or IHE ACM.

Prescribers, homecare providers, nursing providers can be connected together in a health network (cloud environment).

A homecare provider user can create a care plan and associate with the prescriber or prescribing organization. Alternatively, a hospital user can refer a care plan to a home care provider. All actors involved in this care plan will have access and be able to manage the care plan. Home care providers can have access to part of hospital therapies (including the part of the drug library) so that they can create care plans according to the hospital protocols. The hospitals can select which therapies would be accessible by the connected homecare providers.

Organization defined therapy categories and care areas can be associated by the organization with specific care properties. By means of care properties predefined in the system, the presentation of infusion data in the system and the input means of the care plan of a patient are controlled. An example of a care property type is the type of the infusion therapy (post-operative pain, obstetrics pain, parenteral nutrition, general infusion). Other care property types could be the route of administration, the catheter type etc.

A creation and control of care plans (cf. FIG. 3c) for the patient can be provided which define a monitoring and control session for the specific patient and groups orders, devices, alarms, infusion and other therapy data. A care plan and infusion order defines the remaining two items of the 5R rule by adding the name of the right patient and the right time to infuse to the contents of the drug library which, as mentioned above, only fulfills the other three items of the 5R rule.

A manual association of a patient care plan can be provided through an application interface directly with the care properties in the system or indirectly through the association of the care plan with therapy categories or care areas. Associated therapies or care areas of a given care plan can be changed based on the therapy status or progress of the hospitalization. Specifically, the care area associated with the care plan can be automatically changed based on location information from the pump or information received from external systems.

Multiple concurrent care plans can be created for a patient. For example, a care plan for general infusion will be created for a patient under surgery, and a new care plan will be created dedicated to the pain management.

An automatic creation of care plan can be carried out based on operator actions on the pump interface for a new patient programming through drug or protocol library. In case the patient identification information is available at the point of care, the care plan will be associated with the given patient, else the care plan will be associated with an anonymous patient at creation and the actual patient can be manually assigned through the application interface after creation of the care plan. Multiple infusions and infusion pumps can be automatically associated with a care plan (for care plans defined with care area) based on information about the patient and the care area received from the pump.

A manual or automatic association of therapy questionnaires defined in the system for the selected therapy to the care plan is provided. There is an option to terminate the care plan on the pump interface when a new therapy is selected or when a new patient is selected. The care plan can be terminated manually by the user through the user interface of the terminals.

Infusion orders (e-prescription) are done through application interface (could be at the point of care through a mobile application interface). A creation of infusion orders in an application interface can be done from a scratch or through selecting, copying and editing protocols defined in the drug library or protocol library wherein an optional association to a care plan can be provided. In case the prescription is based on the drug library or protocol library, the safety limits apply. The infusion order includes a part or all of the information for a 5R verification (including the time to be delivered and route of administration). Patient specific delivery programming limits can be defined in the infusion order for a local (at the pump) and/or remote modification of the protocol. A special custom formulation of drugs and fluids can be defined in the infusion order. As an example, parenteral nutrition formulation can be defined, and the associated nutrient content can be calculated automatically or manually defined. The infusion orders can be also automatically entered in the system by external HIT systems wherein the interoperability for example can use the integrated health care enterprise point-of-care infusion verification (IHE PIV) profile. Infusion orders created through the system interface could be communicated to external HIT systems. An infusion order can be valid for a single or multiple or unlimited number of infusions, and can define the intervals of the repeating infusions (e.g. 2 infusions per month). Multiple infusion orders can be grouped to be applied on a single pump as pump protocol group. The infusion order or pump protocol group can include device settings (like pump alarm settings) as defined in the system for the related therapy or care area or protocol group. The infusion orders can have time/completion relation between each other. Multiple infusion orders can be created per patient or care plan. There can be provided templates for a quick creation of multiple infusion orders that contain the inter-relations of the orders. Those include sequential and concurrent infusion orders for a single pump or stack of pumps.

Further provided is the printing of barcode and RFID tags for drugs contained in a master drug list or specified in the infusion orders. A list of medications pending to be dispensed is presented in the user interface. Each drug prepared and stored in the pharmacy or dispensed from the pharmacy is tracked in the system with manual input or by RFID or barcode scanning.

Pending orders for a patient are shown in a timetable together with infused and actual infusion status as known in prior art pharmacy organization.

Further provided is a patient/care plan/infusion order binding to the pump. A patient identification can be done through the application or the pump interface via manual entry, scanning bar code or RFID tag or patient photo and recognition or other identification means or selection from an available patient list and if required in combination with information received from connected third party HIT systems. Manual patient care plan or infusion order association with the pump can be done through the pump interface by selecting the patient from the list of unassociated or active care plans or orders with optional verification with entering a part or all of the elements of the patient identification information (e.g. year of birth). The list is transferred from the server to the pump. Alternatively, patient, care plan or infusion order association with the pump can be done by scanning the patient and/or drug identification information with the pump or with another terminal device connected to the system. If the terminal device is not the pump, the pump ID should be entered or selected manually or by scanning the barcode or RFID of the device.

Further provided is a patient association with a device group. In case at least an infusion order exists for a patient, an automatic verification of the correct match according to the 5R rule between patient, drug, infusion order and time is performed based on information provided from the point of care (drug, patient). An automatic transfer of the infusion order(s) to the pump and an automated application of the infusion order(s) on the pump can be carried out.

In case of a manual pump programming, the program is transmitted to the server and verified against the related infusion order(s). In case a mismatch is detected in the drug, route of administration, time of infusion, patient and delivery parameters, an alarm is generated by the system. Optionally the pump also displays an alarm and optionally does not allow the delivery.

There can be an automatic transfer and application of the questionnaires associated with the care plan to the associated pump.

The infusion orders may contain information related to device settings as defined in the application for the specific therapy category. The device can be dissociated from an infusion order or care plan manually through the user interface of the terminals and/or based on identified device location (e.g. if the pump is to be returned to the pool of pumps or a warehouse) and/or based on a time-out after power off (e.g. 24 hours). As expressed, this setting is configurable per care area or therapy.

Each infusion order is related with the respective infusion (medication administration) information received by the device. The compliance of the prescription can be automatically checked and presented not only at the start of the infusion, but throughout the infusion and the therapy. Each medication dispensing event is related with the respective infusion (medication administration) information received by the device allowing traceability between the dispensed and administered medications.

A main screen "Care view" for all therapies and care areas displays the active care plans infusion status (drug infused, infusion status, infusion rate) and alarms so as to monitor the therapies (cf. FIG. 3d).

In the user interface the ongoing care plans of a specific therapy along with information relevant to this therapy based on the associated care properties are presented as therapy views. The user can select the therapy to access different views (and filter the presented care plans). The ongoing care plans identified by the patient information and therapy are presented as lines and the therapy information as columns of a table. In case of information that is based on aggregation (e.g. number of patient bolus requested over a period), the relative aggregation range can be selected by the user (e.g. last 12 hours). The information presented in the columns of each therapy can be system default (based on the care properties) or defined be the user. The user can create customized views by selecting the care properties of each custom view and the columns for each view. The user can define the view that is presented when the "therapy views" is accessed.

The therapy monitoring screen (cf. FIG. 3d) for each care plan (cf. FIG. 3c) depends on the care properties associated with each care plan.

The alarms can be active alarms and/or history alarms.

A patient bolus activity can comprise information about the bolus requested and the bolus given for the period selected by the user. Trends and aggregated data per day of week for bolus requested or given per hour, line pressure, delivered drug/fluids can be displayed. Especially for palliative care the bolus requested or given per hour is displayed on the same graph with a horizontal axis representing the hour of the day for a selected period (e.g. a week). This allows the user to identify a pattern of pain related to the hour of the day. Specifically for parenteral nutrition (PN) and enteral nutrition (EN) a breakdown for nutrient elements can be observed, based on the nutrient content that has been defined for the fluids in the drug list.

Infusions (administered medication) are presented in relation to the prescription to demonstrate the level of prescription adherences in time graphs and table reports.

The fluid balance of the patient per day or other selected time period is presented by the infusion data and observations related to the patient fluid output.

The Infusion timeline view allows to monitor the completed, ongoing and pending/ordered infusions in time. The data from infusions, pending orders and feedback mechanisms are presented grouped per patient, care plan and order. The user can select and save filters with criteria like completed, executing, pending infusions, care area etc. The patient location and the summary of active alarms are also displayed. The delivered drug can be presented in frames of user selected time windows (e.g. 10 minutes). Alarms can be shown on the floor plan of the organization (that includes the beds) as room alarms.

As action lists provided can be Alarms (cf. FIG. 3e)-Pending orders list (ordered by time)-Infusions near end-Pending orders ordered by time-Questionnaires.

There is a list of alarms that require handling order by descending priority and grouped by patient, the infusion remaining time ordered by remaining time, the pending orders ordered by due time, and the questionnaires that require feedback ordered by time passed from trigger time.

The system allows the creation of custom notes under the context of a specific care plan. The notes can include a "@" reference in which case the note is sent as a message to other users including the care plan context.

The terminal through which an infusion can be programmed can automatically filter the data presented based on its location (e.g. present only patients close to the terminal).

For a continuous quality improvement (CQI) the pump can send events for exceeding the defined delivery safety limit (hard or soft) and the programming method per infusion (auto-verification, drug library, protocol library or manual). The system based on the pump data provides statistic reports per care area, profile and drug for drug usage, soft and hard overrides (including the limit, the attempted value and overridden or corrected (for soft)), programming method, delays to execute infusions and responsiveness to address alarms.

Since an access of an operator can be tracked by RFID or barcode or another identification system, above reports can be provided by the operator and support the healthcare personnel training and performance monitoring. Therapy related information and satisfactions scores from observations can provide an overview of the care delivered. The CQI data can be compared with similar data from other organizations, allowing a better understanding to an organization about the quality of its operations.

The user can browse the local drug library or alternatively, since the pump is an alternative terminal of the system, connect to the drug library of the system. The user interface can be indicative for browsing the drug library (cf. FIG. 3b).

For a device management the system offers to the user of the organization a real time report about the registered devices with information about the software version, drug library version, preventive maintenance due date, utilization and location. This information can also be transmitted to third party systems through interoperability profiles. Areas for pump storage and their associated WiFi signature can be defined. Technical service actions performed on the device like preventive maintenance or service of a defect can be tracked in the system.

A "Find pumps location" menu to be displayed e.g. on the screen 411 of the computer 41 (wherein such a screen has the function of an output unit) shows all departments and care areas where pumps are used or stored, even outside the hospital, (cf. EP 2 881 875 A1 or US 2015/0112265 A1) by using a hospital map or Google Maps (for external).

FIGS. 4a to 4i illustrate examples of pages and windows in particular to be shown on the screen 161 of the mobile device 16 and/or on the screen 411 of the computer 41.

FIG. 4a shows a page indicating the patient bolus activity with information about the bolus requested and given for a period selected by the user.

Figure 4B:
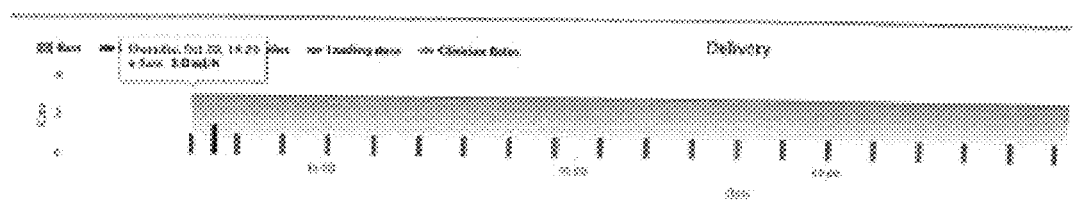

FIG. 4b shows a page including a graph of observations for the bolus requested and given per hour and the line pressure wherein trends and aggregated data per day of week for the bolus requested and given per hour, the line pressure and the delivered drugs can be determined from this graph.

Figure 4C:
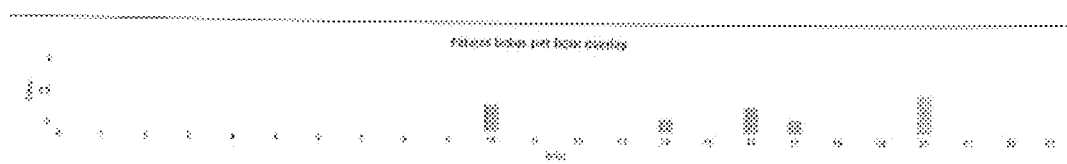

Especially for palliative care, the bolus requested and given per hour is displayed on the same graph with the horizontal axis representing the hour of the day for a selected period (e.g. a week) as shown in FIG. 4c, so that the user is allowed to identify a pattern of pain related to the hour of the day.

Figure 4D:
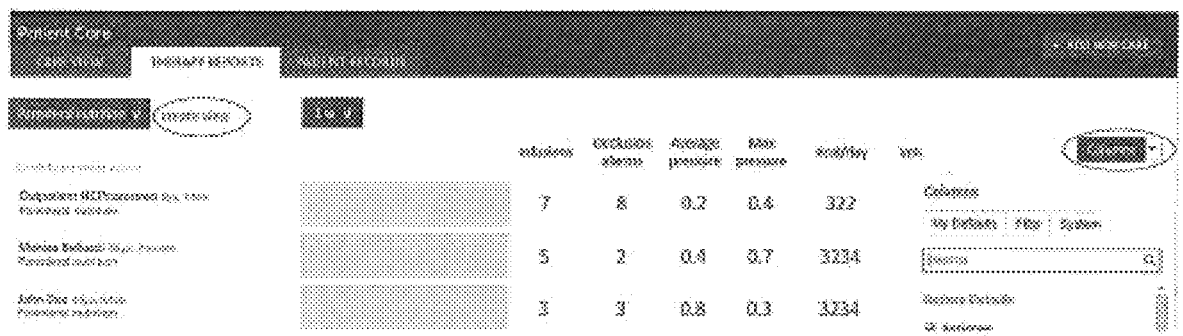

FIG. 4d exemplarily illustrates a multiple patient window with therapy views. In this user interface the ongoing care plans of a specific therapy along with information relevant to this therapy based on the associated care properties are presented.

The user can select the therapy to access different views (and filter the presented care plans). The ongoing care plans identified by the patient information and therapy are presented as lines and the therapy information as columns of a table. In case of information that is based on aggregation (e.g. number of patient bolus requested over a period) the relative aggregation range can be selected by the user (e.g. last 12 hours). The information presented in the columns of each therapy can be system default (base on the care properties) or defined be the user. The user can create custom views by selecting the care properties of each custom view and the columns for each view. The user can define the view that is presented when the "therapy views" is accessed. The therapy monitoring screen for each care plan depends on the care properties associated with each care plan.

Figure 4E:
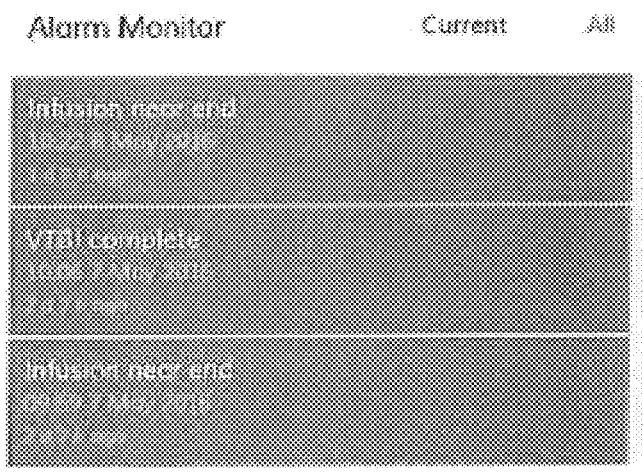

FIG. 4e shows an alarm window indicating active alarms and the history of alarms.

Figures 4F, 4G:
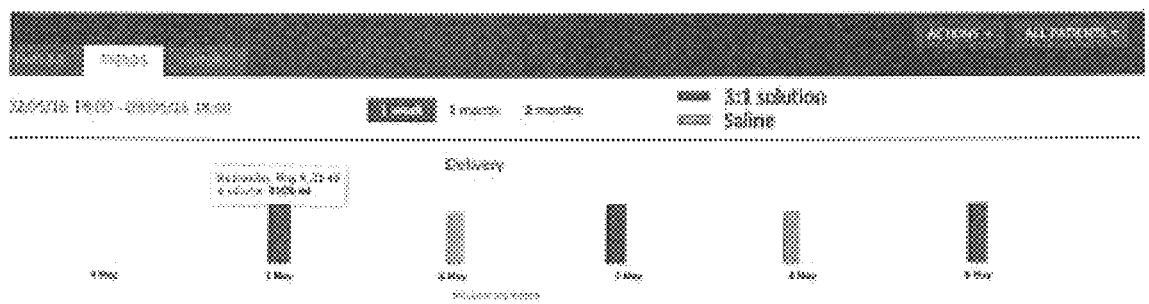

FIGS. 4f and 4g illustrate parenteral/enteral nutrition pages wherein the page according to FIG. 4g includes a graph. In particular for parenteral nutrition and enteral nutrition, it must be taken care of a breakdown for nutrition elements based on the nutrient content that has been defined for the fluids in the drug list.

Infusions (administered medication) are presented in relation to the prescription to demonstrate the level of prescription adherences in time graphs and table reports.

Figure 4H:
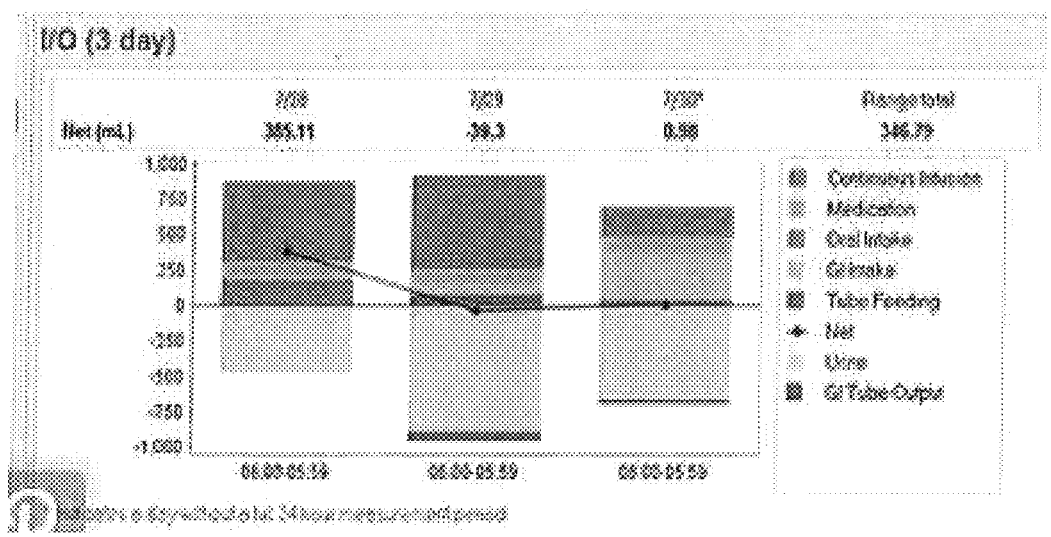

The fluid balance of the patient per day or other selected time period is presented by the infusion data and observations related to the patient fluid output as given on the page shown in FIG. 4h.

Figure 4I:
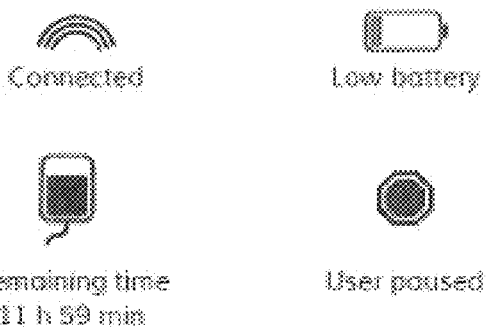

FIG. 4i shows a window for monitoring the pump status (for all care types).

Finally, as a further example two scenarios are given:
Scenario 1:
Therapy: Peripheral nerve block
Care Type: Post Operative Pain
Profile: Femoral Block
Questions: VAS score Scale 1-10 Alarm @ 6
   Numbness Y/N Alarm @ Y
One Drug of many: Ropivacaine 1 mg/ml
Database gives Protocol: Basal rate 2 ml/h
   Bolus 1 ml
   Lockout time 10 min
   Delivery route peripheral nerve
   Device settings near EOI 3 ml, occ pressure high
Shows: answers to questions, red alarm if activated from levels, pump function/pump alarms and connectivity.
Scenario 2:
Therapy: Parenteral Nutrition
Care Type: Parenteral Nutrition
Profile: Adult
Questions:
One Drug of many: Total Parenteral Nutrition
   Carbohydrates: 7000 Kcal/L
   Lipids: 3000 Kcal/L
   Protein: 700 Kcal·L
Database gives Protocol: Basal rate: 160 ml/h
   Feedback: Downstream Pressure Monitoring
   Occlusions per infusion alarm: 5
   Occlusions summed time: 3 min
   Delivery route: IV Central Venous Catheter
   Device settings: near EOI 10 ml, occ pressure low
Shows: answers to questions, red alarm if activated from levels, pump function/pump alarms and connectivity.

Finally, it should be noted that the above described embodiment is of an example for implementing the present invention. However, the scope of the present invention should not necessarily be limited by the above description, but is defined by the following claims:

The invention claimed is:

1. An infusion pump system comprising:
   a pump adapted to be attached to a patient, to cause infusion of a drug into the patient's body, and to receive therapy feedback data;
   a server, communicatively coupled to the pump, and adapted to store a plurality of therapy data representing different therapies, a plurality of drug data representing different drugs, a plurality of protocol data representing different protocols each of which defines a specific drug delivery and/or application to a patient, a plurality of profile data representing different profiles relating to specificities relevant for a therapy, wherein the specificities relevant for the therapy comprise patient attributes, delivery attributes, and route attributes, the route attributes comprising at least one of an intravenous block or a brachial block, a plurality of care type data representing specific aspects of therapies, a plurality of alarm data comprising catheter blockage alarm data wherein the server is configured to identify the catheter blockage alarm data from the plurality of alarm data when a pump feedback data comprises a predetermined number of occlusion alarm data indicating a predetermined number of temporary interrupts of operation of the pump within a predetermined time period, and a plurality of therapy feedback data including information about particularities of therapies already carried out or currently running;
a terminal device, communicatively coupled to the server and the pump, and adapted to enable a selection of specific therapy data representing a specific therapy from said plurality of therapy data, specific drug data representing a specific drug from said plurality of drug data, specific profile data representing a specific profile from said plurality of profile data, and specific care type data from said plurality of care type data, the terminal device further configured to generate a catheter blockage alarm when the pump feedback data comprises a number of occlusion alarms indicating a number of temporary interrupts of operation of the pump, the number of occlusion alarms exceeding a threshold number identified in the catheter blockage alarm data;
wherein said server is further adapted to provide an association of the selected specific therapy data, the selected specific drug data, the selected specific profile data and the selected specific care type data provided by said terminal device and further adapted to determine on the basis of said association specific protocol data representing a specific protocol from said plurality of protocol data and specific therapy feedback data representing a specific therapy feedback from said plurality of therapy feedback data, as well as to store said association along with said specific protocol data and said specific therapy feedback data; and
wherein said terminal device is further adapted to output said specific protocol data along with said specific therapy feedback data, program the pump in accordance with the specific protocol data and to adjust the programming of the pump in accordance with the therapy feedback data;
wherein said terminal device is further adapted to select a specific monitoring page format comprising predetermined fields, from a plurality of pre-determined monitoring page formats, based on the specific care type data; and
wherein said terminal device is further adapted to generate a monitoring page based on the specific monitoring page format and comprising therapy feedback data and adapted to be shown on a display.

2. The system according to claim 1, wherein said terminal device is further adapted to enable input of updated therapy feedback data for a given therapy, drug, profile and/or care type; and
said server is further adapted to replace current therapy feedback data by said updated therapy feedback data for said given therapy, drug, profile and/or care type and/or a current status of said pump.

3. The system according to claim 1, wherein said server is a remote server, said terminal device is included in said pump, and said remote server is connected to said pump.

4. The system according to claim 1, wherein said server is a remote server, and said terminal device is included in the remote server, and said remote server is connected to said pump.

5. The system according to claim 1, wherein said terminal device comprises a display to indicate the output from said terminal device.

6. The system according to claim 1, wherein the terminal device comprises a display to indicate operational data of said pump.

7. The system according to claim 6, wherein the terminal device is at least one of a personal computer, a notebook, a tablet computer, a mobile telephone, and a mobile device.

8. The system according to claim 1, wherein said terminal device is adapted to provide questions regarding the selected specific therapy and to provide answers to said questions as therapy feedback.

9. The system according to claim 8, wherein said terminal device is further adapted to provide one or several proposed answers of each question, and said terminal device is adapted to enable to select a proposed answer to a question as therapy feedback.

10. The system according to claim 8, wherein when the specific care type data relates to a palliative care pain, the terminal device is adapted to provide at least a question of visual analog scale pains score at rest.

11. The system according to claim 8, wherein when the specific care type data relates to a post-operative pain, the terminal device is adapted to provide at least one of a question of visual analog scale pain score at rest, visual analog scale pain score at mobilization, numbness, motor blockage, and satisfaction with regard to the specific patient.

12. The system according to claim 8, wherein the terminal device is adapted to provide a question of nutrition content data for any nutrient type data when inputting therapy data and drug data.

13. The system according to claim 8, wherein the questions are presented to the patient in response to the infusion of the drug into the patient's body.

14. The system according to claim 1, wherein said server is further adapted to store a plurality of nutrient type data representing different types of nutrient and a plurality of nutrient content data representing different contents of nutrient, wherein specific nutrient content data representing a specific content of nutrient from said plurality of nutrient content data for specific nutrient type data representing a specific type of nutrient from said plurality of nutrient type data are linked to specific therapy data representing a specific therapy from said plurality of therapy data and to specific drug data representing a specific drug from said plurality of drug data.

15. The system according to claim 14, wherein said terminal device is further adapted to enable an input of at least therapy data and drug data for storing in said server, when the specific care type data relates to an enteral or parenteral nutrition, said terminal device is further adapted to enable an input of nutrient type data and nutrient content data for storing in said server, and said terminal device is further adapted to output specific nutrient content data, including per time unit, in accordance with the selected specific therapy and drug data.

16. The system according to claim 1, wherein said plurality of drug data includes data representing desired safety limits for a stored drug, including in accordance with specific protocol data.

17. The system according to claim 1, wherein said server is further adapted to store a plurality of patient category data which differ from each other at least with regard of gender, age, bodyweight, and disease severity, wherein, in accordance with specific therapy data representing a specific therapy from said plurality of therapy data and further in accordance with specific patient category data representing a specific patient category from said plurality of patient category data, specific protocol data representing one or more specific protocols from said plurality of protocol data and including specific time-to-infuse data and/or specific delivery route data are linked to specific profile data representing a specific profile from said plurality of profile data.

18. The system according to claim 1, wherein said display is provided at a remote device.

19. The system according to claim 1, wherein said server is further adapted to associate protocol data representing several different specific protocols to therapy data representing one or more specific therapies.

20. The system according to claim 1, wherein said server is further adapted to store a plurality of care area data representing different care areas,
    said terminal device is further adapted to enable a selection of specific care area data representing a specific care area from said plurality of care area data, and said server is further adapted to incorporate the selected specific care area data into said association.

21. The system according to claim 20, wherein said server is further adapted to associate protocol data representing specific concurrent and sequential protocols to therapy data representing one or more specific therapies, drug data representing one or more specific drugs, and care area data representing one or more care areas.

22. The system according to claim 1, wherein said plurality of alarm data include pump alarm data representing different pump related alarms.

23. The system according to claim 1, wherein said server is further adapted to store a plurality of feedback level data representing different levels for feedback data, and said server is further adapted to determine on the basis of said association specific feedback level data representing a specific level from said plurality of feedback level data.

24. The system according to claim 1, wherein said terminal device is further adapted to generate a time graph that provides the drug adherence of the drug over a period of time during which the drug is administered.

25. The system according to claim 1, further comprising an additional pump associated with the patient, the additional pump being configured to cause infusion of an additional drug into the patient's body.

26. The system according to claim 1, wherein said terminal device is further adapted to determine the location of the pump and generate an alarm based on the location of the pump being different than predetermined locations.

27. An infusion pump system comprising:
    a pump adapted to be attached to a patient, to cause infusion of a drug into the patient's body, and to receive therapy feedback data;
    a server, communicatively coupled to the pump, and adapted to store a plurality of therapy data representing different therapies, a plurality of drug data representing different drugs, a plurality of protocol data representing different protocols each of which defines a specific drug delivery and/or application to a patient, a plurality of profile data representing different profiles relating to specificities relevant for a therapy, wherein the specificities relevant for the therapy comprise patient attributes, delivery attributes, and route attributes, the route attributes comprising at least one of an intravenous block or a brachial block, a plurality of care type data representing specific aspects of therapies, a plurality of alarm data comprising catheter blockage alarm data wherein the server is configured to identify the catheter blockage alarm data from the plurality of alarm data when a pump feedback data comprises a predetermined number of occlusion alarm data indicating a predetermined number of temporary interrupts of operation of the pump within a predetermined time period, a plurality of therapy feedback data including information about particularities of therapies already carried out or currently running, and a plurality of nutrient type data representing different types of nutrient and a plurality of nutrient content data representing different contents of nutrient, wherein specific nutrient content data representing a specific content of nutrient from said plurality of nutrient content data for specific nutrient type data representing a specific type of nutrient from said plurality of nutrient type data are linked to specific therapy data representing a specific therapy from said plurality of therapy data and to specific drug data representing a specific drug from said plurality of drug data;
    a terminal device, communicatively coupled to the server and the pump, and adapted to enable a selection of specific therapy data representing a specific therapy from said plurality of therapy data, specific drug data representing a specific drug from said plurality of drug data, specific profile data representing a specific profile from said plurality of profile data, and specific care type data from said plurality of care type data, the terminal device further configured to generate a catheter blockage alarm when the pump feedback data comprises a number of occlusion alarms indicating a number of temporary interrupts of operation of the pump, the number of occlusion alarms exceeding a threshold number identified in the catheter blockage alarm data;
    wherein said server is further adapted to provide an association of the selected specific therapy data, the selected specific drug data, the selected specific profile data and the selected specific care type data provided by said terminal device and further adapted to determine on the basis of said association specific protocol data representing a specific protocol from said plurality of protocol data and specific therapy feedback data representing a specific therapy feedback from said plurality of therapy feedback data, as well as to store said association along with said specific protocol data and said specific therapy feedback data; and
    wherein said terminal device is further adapted to output said specific protocol data along with said specific therapy feedback data, program the pump in accordance with the specific protocol data and to adjust the programming of the pump in accordance with the therapy feedback data;
    wherein said terminal device is further adapted to select a specific monitoring page format comprising predetermined fields, from a plurality of pre-determined monitoring page formats, based on the specific care type data; and
    wherein said terminal device is further adapted to generate a monitoring page based on the specific monitoring page format and comprising therapy feedback data and adapted to be shown on a display, provide questions regarding the selected specific therapy, and provide answers to said questions as therapy feedback.

28. An infusion pump system comprising:
    a pump adapted to be attached to a patient, to cause infusion of a drug into the patient's body, and to receive therapy feedback data;

a server, communicatively coupled to the pump, and adapted to store a plurality of therapy data representing different therapies, a plurality of drug data representing different drugs, a plurality of protocol data representing different protocols each of which defines a specific drug delivery and/or application to a patient, a plurality of profile data representing different profiles relating to specificities relevant for a therapy, wherein the specificities relevant for the therapy comprise patient attributes, delivery attributes, and route attributes, the route attributes comprising at least one of an intravenous block or a brachial block, a plurality of care type data representing specific aspects of therapies, a plurality of alarm data comprising catheter blockage alarm data wherein the server is configured to identify the catheter blockage alarm data from the plurality of alarm data when a pump feedback data comprises a predetermined number of occlusion alarm data indicating a predetermined number of temporary interrupts of operation of the pump within a predetermined time period, the plurality of care type data representing specific aspects of therapies chosen from post-operative pain, palliative care, parenteral nutrition, post-operative pain regional, obstetric pain, chemotherapy, antibiotherapy, immunotherapy, primary pulmonary hypertension, concurrent infusions, sequential infusions, or combinations thereof, a plurality of alarm data representing different types, levels, or both, of an alarm, said plurality of alarm data including catheter blockage alarm data, a plurality of therapy feedback data including information about particularities of therapies already carried out or currently running, said plurality of therapy feedback data including occlusion alarm data received from said pump and indicating a temporary interruption of operation of said pump, and a plurality of nutrient type data representing different types of nutrient and a plurality of nutrient content data representing different contents of nutrient, wherein specific nutrient content data representing a specific content of nutrient from said plurality of nutrient content data for specific nutrient type data representing a specific type of nutrient from said plurality of nutrient type data are linked to specific therapy data representing a specific therapy from said plurality of therapy data and to specific drug data representing a specific drug from said plurality of drug data;

a terminal device, communicatively coupled to the server and the pump, and adapted to enable a selection of specific therapy data representing a specific therapy from said plurality of therapy data, specific drug data representing a specific drug from said plurality of drug data, specific profile data representing a specific profile from said plurality of profile data, and specific care type data from said plurality of care type data, the terminal device further configured to generate a catheter blockage alarm when the pump feedback data comprises a number of occlusion alarms indicating a number of temporary interrupts of operation of the pump, the number of occlusion alarms exceeding a threshold number identified in the catheter blockage alarm data;

wherein said server is further adapted to provide an association of the selected specific therapy data, the selected specific drug data, the selected specific profile data and the selected specific care type data provided by said terminal device and further adapted to determine on the basis of said association specific protocol data representing a specific protocol from said plurality of protocol data, specific therapy feedback data representing a specific therapy feedback from said plurality of therapy feedback data and said catheter blockage alarm data from said plurality of alarm data in case said specific feedback data includes a predetermined number of occlusion alarm data indicating a predetermined number of temporary interruptions of operation of said pump within a predetermined time period, as well as to store said association along with said specific protocol data and said specific therapy feedback data; and wherein said terminal device is further adapted to output said specific protocol data along with said specific therapy feedback data, program the pump in accordance with the specific protocol data and to adjust the programming of the pump in accordance with the therapy feedback data;

wherein said terminal device is further adapted to select a specific monitoring page format, comprising predetermined fields, from a plurality of pre-determined monitoring page formats, based on the specific care type data; and wherein said terminal device is further adapted to generate a monitoring page based on the specific monitoring page format and comprising therapy feedback data and adapted to be shown on a display, provide questions regarding the selected specific therapy, and provide answers to said questions as therapy feedback.

29. An infusion pump system comprising:
a pump adapted to be attached to a patient, to cause infusion of a drug into the patient's body, and to receive therapy feedback data;
a server, communicatively coupled to the pump, and adapted to store a plurality of therapy data representing different therapies, a plurality of drug data representing different drugs, a plurality of protocol data representing different protocols each of which defines a specific drug delivery and/or application to a patient, a plurality of profile data representing different profiles relating to specificities relevant for a therapy, wherein the specificities relevant for the therapy comprise patient attributes, delivery attributes, and route attributes, the route attributes comprising at least one of an intravenous block or a brachial block, a plurality of care type data representing specific aspects of therapies, a plurality of alarm data comprising catheter blockage alarm data wherein the server is configured to identify the catheter blockage alarm data from the plurality of alarm data when a pump feedback data comprises a predetermined number of occlusion alarm data indicating a predetermined number of temporary interrupts of operation of the pump within a predetermined time period, and a plurality of therapy feedback data including information about particularities of therapies already carried out or currently running;
a terminal device, communicatively coupled to the server and the pump, and adapted to enable a selection of specific therapy data representing a specific therapy from said plurality of therapy data, specific drug data representing a specific drug from said plurality of drug data, specific profile data representing a specific profile from said plurality of profile data, and specific care type data from said plurality of care type data, the terminal device further configured to generate a catheter blockage alarm when the pump feedback data comprises a number of occlusion alarms indicating a number of temporary interrupts of operation of the pump, the number of occlusion alarms exceeding a threshold number identified in the catheter blockage alarm data;

an automatic pump control configured to adjust dosage of the drug using one or more neural networks, wherein the automatic pump control is further configured to generate an error indication based on a difference between a desired therapy result and a current therapy result exceeding a threshold;

wherein said server is further adapted to provide an association of the selected specific therapy data, the selected specific drug data, the selected specific profile data and the selected specific care type data provided by said terminal device and further adapted to determine on the basis of said association specific protocol data representing a specific protocol from said plurality of protocol data and specific therapy feedback data representing a specific therapy feedback from said plurality of therapy feedback data, as well as to store said association along with said specific protocol data and said specific therapy feedback data; and wherein said terminal device is further adapted to output said specific protocol data along with said specific therapy feedback data, program the pump in accordance with the specific protocol data and to adjust the programming of the pump in accordance with the therapy feedback data.

* * * * *